US011560421B2

(12) United States Patent
Shioda et al.

(10) Patent No.: US 11,560,421 B2
(45) Date of Patent: Jan. 24, 2023

(54) BROAD-SPECTRUM MONOCLONAL ANTIBODIES AGAINST CHIKUNGUNYA VIRUS E1 STRUCTURAL PROTEIN

(71) Applicants: OSAKA UNIVERSITY, Suita (JP); MAHIDOL UNIVERSITY, Nakhon Pathom (TH)

(72) Inventors: Tatsuo Shioda, Osaka (JP); Emi Nakayama, Osaka (JP); Tadahiro Sasaki, Osaka (JP); Orapim Puiprom, Osaka (JP); Aekkachai Tuekprakhon, Bangkok (TH); Pornsawan Leaungwutiwong, Bangkok (TH); Natthanej Luplertlop, Bangkok (TH)

(73) Assignees: Osaka University, Osaka (JP); Mahidol University, Nakhon Pathom (TH)

( * ) Notice: Subject to any disclaimer, the term of this patent is extended or adjusted under 35 U.S.C. 154(b) by 0 days.

(21) Appl. No.: 16/968,470

(22) PCT Filed: Feb. 8, 2019

(86) PCT No.: PCT/JP2019/004667
§ 371 (c)(1),
(2) Date: Aug. 7, 2020

(87) PCT Pub. No.: WO2019/156223
PCT Pub. Date: Aug. 15, 2019

(65) Prior Publication Data

US 2020/0399349 A1 Dec. 24, 2020

(30) Foreign Application Priority Data

Feb. 9, 2018 (JP) ............................ JP2018-022084

(51) Int. Cl.
*C07K 16/10* (2006.01)
*G01N 33/569* (2006.01)

(52) U.S. Cl.
CPC ... *C07K 16/1081* (2013.01); *G01N 33/56983* (2013.01); *C07K 2317/33* (2013.01); *C07K 2317/565* (2013.01); *C12N 2770/36111* (2013.01)

(58) Field of Classification Search
CPC .................................................. C07K 16/1081
See application file for complete search history.

(56) References Cited

U.S. PATENT DOCUMENTS

| | | | | |
|---|---|---|---|---|
| 8,324,352 B2 * | 12/2012 | Carroll | C07K 7/08 424/139.1 |
| 9,376,485 B2 * | 6/2016 | Wang | A61P 37/02 |
| 10,301,392 B2 * | 5/2019 | Chen | C07K 16/2878 |
| 10,577,419 B2 * | 3/2020 | Gauthier | A61P 35/00 |
| 2011/0143333 A1 | 6/2011 | Brehin et al. | |
| 2013/0251744 A1 | 9/2013 | Ueno et al. | |
| 2016/0040134 A1 | 2/2016 | Akahata et al. | |
| 2016/0090403 A1 | 3/2016 | Ueno et al. | |
| 2019/0162727 A1 | 5/2019 | Suzuki et al. | |

FOREIGN PATENT DOCUMENTS

| | | |
|---|---|---|
| JP | 2010-538291 | 12/2010 |
| JP | 2015-508648 | 3/2015 |
| JP | 2015-532090 | 11/2015 |
| JP | 2017-523796 | 8/2017 |
| JP | 2017-207335 | 11/2017 |
| JP | 2019-138777 | 8/2019 |
| WO | 2014/049094 | 4/2014 |
| WO | 2016/168417 | 10/2016 |

OTHER PUBLICATIONS

Tiller, K. E. and P. M. Tessier, Aug. 2015, Advances in Antibody Design, Annu. Rev. Biomed. Eng. 17:191-216.*
Tiller, K. E., et al., 2017a, Arginine mutations in antibody complementarity-determining regions display context-dependent affinity/specificity trade-offs, J. Biol. Chem. 292(40):16638-16652.*
Tiller, K. E., et al., 2017b, Facile affinity maturation of antibody variable domain using natural diversity mutagenesis, Front. Immunol. 8:Article 986, pp. 1-16.*
Tuekprakhon et al., "Variation at position 350 in the Chikungunya virus 6K-E1 protein determines the sensitivity of detection in a rapid E1-antigen test", Scientific Reports, vol. 8, Article No. 1094 (2018).
Masrinoul et al., "Monoclonal antibody targeting chikungunya virus envelope 1 protein inhibits virus release", Virology, pp. 111-117 (2014).
Okabayashi et al., "Detection of Chikungunya Virus Antigen by a Novel Rapid Immunochromatographic Test", JCM, vol. 53, No. 2, pp. 382-388 (2015) (with Author Correction).
Huits et al., "Diagnostic accuracy of a rapid E1-antigen test for chikungunya virus infection in a reference setting", Clinical Microbiology and Infection, vol. 24, pp. 78-81 (2018).
International Search Report and Written Opinion issued for PCT/JP2019/004755, dated May 7, 2019, 9 pages including English translation of the International Search Report.
International Search Report and Written Opinion issued for PCT/JP2019/004667, dated Apr. 2, 2019, 7 pages including English translation of the International Search Report.

* cited by examiner

*Primary Examiner* — Jeffrey S Parkin
(74) *Attorney, Agent, or Firm* — Hamre, Schumann, Mueller & Larson, P.C.

(57) ABSTRACT

The present invention provides a new antibody against ECSA type Chikungunya virus, WA type Chikungunya virus, and Asian type Chikungunya virus or an antigen-binding fragment of the antibody. The antibody against Chikungunya virus or the antigen-binding fragment of the antibody of the present invention includes a heavy chain variable region or a heavy chain (1), (2), or (3) and a light chain variable region or a light chain (4).

6 Claims, 2 Drawing Sheets

Specification includes a Sequence Listing.

Reactivity against Sindbis virus (A) 3D11

(B) 13H11

(C) 15B2

(D) CK119

```
                        SEQUENCE LISTING


<160> NUMBER OF SEQ ID NOS: 23

<210> SEQ ID NO 1
<211> LENGTH: 8
<212> TYPE: PRT
<213> ORGANISM: Artificial Sequence
<220> FEATURE:
<223> OTHER INFORMATION: CDRH1 of 3D11 heavy chain

<400> SEQUENCE: 1
```

Gly Tyr Thr Phe Thr Ser Tyr Trp
1 5

<210> SEQ ID NO 2
<211> LENGTH: 11
<212> TYPE: PRT
<213> ORGANISM: Artificial Sequence
<220> FEATURE:
<223> OTHER INFORMATION: CDRH2 of 3D11 heavy chain

<400> SEQUENCE: 2

Ile Tyr Pro Gly Asp Gly Asp Thr Arg Tyr Thr
1 5 10

<210> SEQ ID NO 3
<211> LENGTH: 7
<212> TYPE: PRT
<213> ORGANISM: Artificial Sequence
<220> FEATURE:
<223> OTHER INFORMATION: CDRH3 of 3D11 heavy chain

<400> SEQUENCE: 3

Ser Tyr Asp Pro Phe Asp Tyr
1 5

<210> SEQ ID NO 4
<211> LENGTH: 8
<212> TYPE: PRT
<213> ORGANISM: Artificial Sequence
<220> FEATURE:
<223> OTHER INFORMATION: CDRH1 of 13H11 heavy chain

<400> SEQUENCE: 4

Gly Tyr Ala Phe Ser Thr Ser Trp
1 5

<210> SEQ ID NO 5
<211> LENGTH: 8
<212> TYPE: PRT
<213> ORGANISM: Artificial Sequence
<220> FEATURE:
<223> OTHER INFORMATION: CDRH2 of 13H11 heavy chain

<400> SEQUENCE: 5

Ile Tyr Pro Gly Asp Gly Asp Thr
1 5

<210> SEQ ID NO 6
<211> LENGTH: 9
<212> TYPE: PRT
<213> ORGANISM: Artificial Sequence
<220> FEATURE:
<223> OTHER INFORMATION: CDRH3 of 13H11 heavy chain

<400> SEQUENCE: 6

Ser Asn Asp Gly Tyr Tyr Val Gly Tyr
1 5

<210> SEQ ID NO 7
<211> LENGTH: 8
<212> TYPE: PRT
<213> ORGANISM: Artificial Sequence
<220> FEATURE:
<223> OTHER INFORMATION: CDRH1 of 15B2 heavy chain

<400> SEQUENCE: 7

-continued

```
Gly Tyr Thr Phe Thr Ser Tyr Tyr
1               5


<210> SEQ ID NO 8
<211> LENGTH: 8
<212> TYPE: PRT
<213> ORGANISM: Artificial Sequence
<220> FEATURE:
<223> OTHER INFORMATION: CDRH2 of 15B2 heavy chain

<400> SEQUENCE: 8

Ile Asn Pro Ser Asn Gly Gly Thr
1               5


<210> SEQ ID NO 9
<211> LENGTH: 10
<212> TYPE: PRT
<213> ORGANISM: Artificial Sequence
<220> FEATURE:
<223> OTHER INFORMATION: CDRH3 of 15B2 heavy chain

<400> SEQUENCE: 9

Gly Tyr Tyr Gly Asn Pro Phe Phe Ala Tyr
1               5                   10


<210> SEQ ID NO 10
<211> LENGTH: 6
<212> TYPE: PRT
<213> ORGANISM: Artificial Sequence
<220> FEATURE:
<223> OTHER INFORMATION: CDRL1 of 3D11, 13H11 and 15B2 light chain

<400> SEQUENCE: 10

Glu Asn Val Val Thr Tyr
1               5


<210> SEQ ID NO 11
<211> LENGTH: 3
<212> TYPE: PRT
<213> ORGANISM: Artificial Sequence
<220> FEATURE:
<223> OTHER INFORMATION: CDRL2 of 3D11, 13H11 and 15B2 light chain

<400> SEQUENCE: 11

Gly Ala Ser
1


<210> SEQ ID NO 12
<211> LENGTH: 9
<212> TYPE: PRT
<213> ORGANISM: Artificial Sequence
<220> FEATURE:
<223> OTHER INFORMATION: CDRL3 of 3D11, 13H11 and 15B2 light chain

<400> SEQUENCE: 12

Gly Gln Gly Tyr Ser Tyr Pro Tyr Thr
1               5


<210> SEQ ID NO 13
<211> LENGTH: 116
<212> TYPE: PRT
<213> ORGANISM: Artificial Sequence
<220> FEATURE:
<223> OTHER INFORMATION: Variable region of 3D11 heavy chain

<400> SEQUENCE: 13

Gln Val Gln Leu Gln Gln Ser Gly Ala Glu Leu Ala Arg Pro Gly Ala
```

-continued

```
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Ser Tyr Asp Pro Phe Asp Tyr Trp Gly Gln Gly Thr Thr Leu
            100                 105                 110

Thr Val Ser Ser
        115


<210> SEQ ID NO 14
<211> LENGTH: 118
<212> TYPE: PRT
<213> ORGANISM: Artificial Sequence
<220> FEATURE:
<223> OTHER INFORMATION: Variable region of 13H11 heavy chain

<400> SEQUENCE: 14

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Thr Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Ser Asn Asp Gly Tyr Tyr Val Gly Tyr Trp Gly Gln Gly Thr
            100                 105                 110

Thr Leu Thr Val Ser Ser
        115


<210> SEQ ID NO 15
<211> LENGTH: 119
<212> TYPE: PRT
<213> ORGANISM: Artificial Sequence
<220> FEATURE:
<223> OTHER INFORMATION: Variable region of 15B2 heavy chain

<400> SEQUENCE: 15

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Gln Arg Pro Gly Gln Gly Leu Glu Trp Ile
        35                  40                  45

Gly Glu Ile Asn Pro Ser Asn Gly Gly Thr Asn Phe Asn Glu Lys Phe
    50                  55                  60
```

-continued

```
Lys Asn Lys Ala Thr Leu Thr Val Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Thr Arg Gly Tyr Tyr Gly Asn Pro Phe Phe Ala Tyr Trp Gly Gln Gly
            100                 105                 110

Thr Leu Val Thr Val Ser Ala
        115


<210> SEQ ID NO 16
<211> LENGTH: 106
<212> TYPE: PRT
<213> ORGANISM: Artificial Sequence
<220> FEATURE:
<223> OTHER INFORMATION: Variable region of 3D11, 13H11 and 15B2 light
      chain

<400> SEQUENCE: 16

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile
            100                 105


<210> SEQ ID NO 17
<211> LENGTH: 446
<212> TYPE: PRT
<213> ORGANISM: Artificial Sequence
<220> FEATURE:
<223> OTHER INFORMATION: 3D11 heavy chain

<400> SEQUENCE: 17

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Ser Tyr Asp Pro Phe Asp Tyr Trp Gly Gln Gly Thr Thr Leu
            100                 105                 110

Thr Val Ser Ser Ala Lys Thr Thr Ala Pro Ser Val Tyr Pro Leu Ala
        115                 120                 125

Pro Val Cys Gly Asp Thr Thr Gly Ser Ser Val Thr Leu Gly Cys Leu
```

-continued

```
    130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
        195                 200                 205

Val Asp Lys Lys Ile Glu Pro Arg Gly Pro Thr Ile Lys Pro Cys Pro
    210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
            260                 265                 270

Gln Ile Ser Trp Phe Val Asn Asn Val Glu Val His Thr Ala Gln Thr
        275                 280                 285

Gln Thr His Arg Glu Asp Tyr Asn Ser Thr Leu Arg Val Val Ser Ala
    290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
        355                 360                 365

Thr Asp Phe Met Pro Glu Asp Ile Tyr Val Glu Trp Thr Asn Asn Gly
    370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg Thr Pro Gly Lys
        435                 440                 445


<210> SEQ ID NO 18
<211> LENGTH: 442
<212> TYPE: PRT
<213> ORGANISM: Artificial Sequence
<220> FEATURE:
<223> OTHER INFORMATION: 13H11 heavy chain

<400> SEQUENCE: 18

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Thr Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Asn Tyr Asn Gly Lys Phe
```

-continued

```
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Ser Asn Asp Gly Tyr Tyr Val Gly Tyr Trp Gly Gln Gly Thr
            100                 105                 110

Thr Leu Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440
```

<210> SEQ ID NO 19
<211> LENGTH: 455
<212> TYPE: PRT
<213> ORGANISM: Artificial Sequence -continued

```
<220> FEATURE:
<223> OTHER INFORMATION: 15B2 heavy chain

<400> SEQUENCE: 19

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Gln Arg Pro Gly Gln Gly Leu Glu Trp Ile
        35                  40                  45

Gly Glu Ile Asn Pro Ser Asn Gly Gly Thr Asn Phe Asn Glu Lys Phe
    50                  55                  60

Lys Asn Lys Ala Thr Leu Thr Val Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Thr Arg Gly Tyr Tyr Gly Asn Pro Phe Phe Ala Tyr Trp Gly Gln Gly
            100                 105                 110

Thr Leu Val Thr Val Ser Ala Ala Lys Thr Thr Pro Pro Ser Val Tyr
        115                 120                 125

Pro Leu Ala Pro Gly Cys Gly Asp Thr Thr Gly Ser Ser Val Thr Leu
    130                 135                 140

Gly Cys Leu Val Lys Gly Tyr Phe Pro Glu Ser Val Thr Val Thr Trp
145                 150                 155                 160

Asn Ser Gly Ser Leu Ser Ser Ser Val His Thr Phe Pro Ala Leu Leu
                165                 170                 175

Gln Ser Gly Leu Tyr Thr Met Ser Ser Ser Val Thr Val Pro Ser Ser
            180                 185                 190

Thr Trp Pro Ser Gln Thr Val Thr Cys Ser Val Ala His Pro Ala Ser
        195                 200                 205

Ser Thr Thr Val Asp Lys Lys Leu Glu Pro Ser Gly Pro Ile Ser Thr
    210                 215                 220

Ile Asn Pro Cys Pro Pro Cys Lys Glu Cys His Lys Cys Pro Ala Pro
225                 230                 235                 240

Asn Leu Glu Gly Gly Pro Ser Val Phe Ile Phe Pro Pro Asn Ile Lys
                245                 250                 255

Asp Val Leu Met Ile Ser Leu Thr Pro Lys Val Thr Cys Val Val Val
            260                 265                 270

Asp Val Ser Glu Asp Asp Pro Asp Val Gln Ile Ser Trp Phe Val Asn
        275                 280                 285

Asn Val Glu Val His Thr Ala Gln Thr Gln Thr His Arg Glu Asp Tyr
    290                 295                 300

Asn Ser Thr Ile Arg Val Val Ser Thr Leu Pro Ile Gln His Gln Asp
305                 310                 315                 320

Trp Met Ser Gly Lys Glu Phe Lys Cys Lys Val Asn Asn Lys Asp Leu
                325                 330                 335

Pro Ser Pro Ile Glu Arg Thr Ile Ser Lys Ile Lys Gly Leu Val Arg
            340                 345                 350

Ala Pro Gln Val Tyr Ile Leu Pro Pro Pro Ala Glu Gln Leu Ser Arg
        355                 360                 365

Lys Asp Val Ser Leu Thr Cys Leu Val Val Gly Phe Asn Pro Gly Asp
    370                 375                 380

Ile Ser Val Glu Trp Thr Ser Asn Gly His Thr Glu Glu Asn Tyr Lys
385                 390                 395                 400
```

Asp Thr Ala Pro Val Leu Asp Ser Asp Gly Ser Tyr Phe Ile Tyr Ser
405 410 415

Lys Leu Asn Met Lys Thr Ser Lys Trp Glu Lys Thr Asp Ser Phe Ser
420 425 430

Cys Asn Val Arg His Glu Gly Leu Lys Asn Tyr Tyr Leu Lys Lys Thr
435 440 445

Ile Ser Arg Ser Pro Gly Lys
450 455

<210> SEQ ID NO 20
<211> LENGTH: 214
<212> TYPE: PRT
<213> ORGANISM: Artificial Sequence
<220> FEATURE:
<223> OTHER INFORMATION: 3D11, 13H11 and 15B2 light chain

<400> SEQUENCE: 20

Asn Ile Val Met Thr Gln Ser Pro Lys Ser Met Ser Met Ser Val Gly
1 5 10 15

Glu Arg Val Thr Leu Thr Cys Lys Ala Ser Glu Asn Val Val Thr Tyr
20 25 30

Val Ser Trp Tyr Gln Gln Lys Pro Glu Gln Ser Pro Lys Leu Leu Ile
35 40 45

Tyr Gly Ala Ser Asn Arg Tyr Thr Gly Val Pro Asp Arg Phe Thr Gly
50 55 60

Ser Gly Ser Ala Thr Asp Phe Thr Leu Thr Ile Ser Ser Val Gln Ala
65 70 75 80

Glu Asp Leu Ala Asp Tyr His Cys Gly Gln Gly Tyr Ser Tyr Pro Tyr
85 90 95

Thr Phe Gly Gly Gly Thr Lys Leu Glu Ile Lys Arg Ala Asp Ala Ala
100 105 110

Pro Thr Val Ser Ile Phe Pro Pro Ser Ser Glu Gln Leu Thr Ser Gly
115 120 125

Gly Ala Ser Val Val Cys Phe Leu Asn Asn Phe Tyr Pro Lys Asp Ile
130 135 140

Asn Val Lys Trp Lys Ile Asp Gly Ser Glu Arg Gln Asn Gly Val Leu
145 150 155 160

Asn Ser Trp Thr Asp Gln Asp Ser Lys Asp Ser Thr Tyr Ser Met Ser
165 170 175

Ser Thr Leu Thr Leu Thr Lys Asp Glu Tyr Glu Arg His Asn Ser Tyr
180 185 190

Thr Cys Glu Ala Thr His Lys Thr Ser Thr Ser Pro Ile Val Lys Ser
195 200 205

Phe Asn Arg Asn Glu Cys
210

<210> SEQ ID NO 21
<211> LENGTH: 981
<212> TYPE: PRT
<213> ORGANISM: Chikungunya virus

<400> SEQUENCE: 21

Met Cys Leu Leu Ala Asn Thr Thr Phe Pro Cys Ser Gln Pro Pro Cys
1 5 10 15

Thr Pro Cys Cys Tyr Glu Lys Glu Pro Glu Glu Thr Leu Arg Met Leu
20 25 30

```
Glu Asp Asn Val Met Arg Pro Gly Tyr Tyr Gln Leu Leu Gln Ala Ser
        35                  40                  45

Leu Thr Cys Ser Pro His Arg Gln Arg Arg Ser Thr Lys Asp Asn Phe
    50                  55                  60

Asn Val Tyr Lys Ala Thr Arg Pro Tyr Leu Ala His Cys Pro Asp Cys
65                  70                  75                  80

Gly Glu Gly His Ser Cys His Ser Pro Val Ala Leu Glu Arg Ile Arg
                85                  90                  95

Asn Glu Ala Thr Asp Gly Thr Leu Lys Ile Gln Val Ser Leu Gln Ile
            100                 105                 110

Gly Ile Lys Thr Asp Asp Ser His Asp Trp Thr Lys Leu Arg Tyr Met
        115                 120                 125

Asp Asn His Met Pro Ala Asp Ala Glu Arg Ala Gly Leu Phe Val Arg
    130                 135                 140

Thr Ser Ala Pro Cys Thr Ile Thr Gly Thr Met Gly His Phe Ile Leu
145                 150                 155                 160

Ala Arg Cys Pro Lys Gly Glu Thr Leu Thr Val Gly Phe Thr Asp Ser
                165                 170                 175

Arg Lys Ile Ser His Ser Cys Thr His Pro Phe His His Asp Pro Pro
            180                 185                 190

Val Ile Gly Arg Glu Lys Phe His Ser Arg Pro Gln His Gly Lys Glu
        195                 200                 205

Leu Pro Cys Ser Thr Tyr Val Gln Ser Thr Ala Ala Thr Thr Glu Glu
    210                 215                 220

Ile Glu Val His Met Pro Pro Asp Thr Pro Asp Arg Thr Leu Met Ser
225                 230                 235                 240

Gln Gln Ser Gly Asn Val Lys Ile Thr Val Asn Gly Gln Thr Val Arg
                245                 250                 255

Tyr Lys Cys Asn Cys Gly Gly Ser Asn Glu Gly Leu Thr Thr Thr Asp
            260                 265                 270

Lys Val Ile Asn Asn Cys Lys Val Asp Gln Cys His Ala Ala Val Thr
        275                 280                 285

Asn His Lys Lys Trp Gln Tyr Asn Ser Pro Leu Val Pro Arg Asn Ala
    290                 295                 300

Glu Leu Gly Asp Arg Gln Gly Lys Ile His Ile Pro Phe Pro Leu Ala
305                 310                 315                 320

Asn Val Thr Cys Arg Val Pro Lys Ala Arg Asn Pro Thr Val Thr Tyr
                325                 330                 335

Gly Lys Asn Gln Val Ile Met Leu Leu Tyr Pro Asp His Pro Thr Leu
            340                 345                 350

Leu Ser Tyr Arg Asn Met Gly Glu Glu Pro Asn Tyr Gln Glu Glu Trp
        355                 360                 365

Val Met His Lys Lys Glu Val Val Leu Thr Val Pro Thr Glu Gly Leu
    370                 375                 380

Glu Val Thr Trp Gly Asn Asn Glu Pro Tyr Lys Tyr Trp Pro Gln Leu
385                 390                 395                 400

Ser Thr Asn Gly Thr Ala His Gly His Pro His Glu Ile Ile Leu Tyr
                405                 410                 415

Tyr Tyr Glu Leu Tyr Pro Thr Met Thr Val Val Val Val Ser Val Ala
            420                 425                 430

Thr Phe Ile Leu Leu Ser Met Val Gly Met Ala Ala Gly Met Cys Met
        435                 440                 445

Cys Ala Arg Arg Arg Cys Ile Thr Pro Tyr Glu Leu Thr Pro Gly Ala
```

-continued

```
    450                 455                 460

Thr Val Pro Phe Leu Leu Ser Leu Ile Cys Cys Ile Arg Thr Ala Lys
465                 470                 475                 480

Ala Ala Thr Tyr Gln Glu Ala Ala Ile Tyr Leu Trp Asn Glu Gln Gln
                485                 490                 495

Pro Leu Phe Trp Leu Gln Ala Leu Ile Pro Leu Ala Ala Leu Ile Val
            500                 505                 510

Leu Cys Asn Cys Leu Arg Leu Leu Pro Cys Cys Cys Lys Thr Leu Ala
        515                 520                 525

Phe Leu Ala Val Met Ser Val Gly Ala His Thr Val Ser Ala Tyr Glu
    530                 535                 540

His Val Thr Val Ile Pro Asn Thr Val Gly Val Pro Tyr Lys Thr Leu
545                 550                 555                 560

Val Asn Arg Pro Gly Tyr Ser Pro Met Val Leu Glu Met Glu Leu Leu
                565                 570                 575

Ser Val Thr Leu Glu Pro Thr Leu Ser Leu Asp Tyr Ile Thr Cys Glu
            580                 585                 590

Tyr Lys Thr Val Ile Pro Ser Pro Tyr Val Lys Cys Cys Gly Thr Ala
        595                 600                 605

Glu Cys Lys Asp Lys Asn Leu Pro Asp Tyr Ser Cys Lys Val Phe Thr
    610                 615                 620

Gly Val Tyr Pro Phe Met Trp Gly Gly Ala Tyr Cys Phe Cys Asp Ala
625                 630                 635                 640

Glu Asn Thr Gln Leu Ser Glu Ala His Val Glu Lys Ser Glu Ser Cys
                645                 650                 655

Lys Thr Glu Phe Ala Ser Ala Tyr Arg Ala His Thr Ala Ser Ala Ser
            660                 665                 670

Ala Lys Leu Arg Val Leu Tyr Gln Gly Asn Asn Ile Thr Val Thr Ala
        675                 680                 685

Tyr Ala Asn Gly Asp His Ala Val Thr Val Lys Asp Ala Lys Phe Ile
    690                 695                 700

Val Gly Pro Met Ser Ser Ala Trp Thr Pro Phe Asp Asn Lys Ile Val
705                 710                 715                 720

Val Tyr Lys Gly Asp Val Tyr Asn Met Asp Tyr Pro Pro Phe Gly Ala
                725                 730                 735

Gly Arg Pro Gly Gln Phe Gly Asp Ile Gln Ser Arg Thr Pro Glu Ser
            740                 745                 750

Lys Asp Val Tyr Ala Asn Thr Gln Leu Val Leu Gln Arg Pro Ala Val
        755                 760                 765

Gly Thr Val His Val Pro Tyr Ser Gln Ala Pro Ser Gly Phe Lys Tyr
    770                 775                 780

Trp Leu Lys Glu Arg Gly Ala Ser Leu Gln His Thr Ala Pro Phe Gly
785                 790                 795                 800

Cys Gln Ile Ala Thr Asn Pro Val Arg Ala Val Asn Cys Ala Val Gly
                805                 810                 815

Asn Met Pro Ile Ser Ile Asp Ile Pro Glu Ala Ala Phe Thr Arg Val
            820                 825                 830

Val Asp Ala Pro Ser Leu Thr Asp Met Ser Cys Glu Val Pro Ala Cys
        835                 840                 845

Thr His Ser Ser Asp Phe Gly Gly Val Ala Ile Ile Lys Tyr Ala Ala
    850                 855                 860

Ser Lys Lys Gly Lys Cys Ala Val His Ser Met Thr Asn Ala Val Thr
865                 870                 875                 880
```

```
Ile Arg Glu Ala Glu Ile Glu Val Glu Gly Asn Ser Gln Leu Gln Ile
                885                 890                 895

Ser Phe Ser Thr Ala Leu Ala Ser Ala Glu Phe Arg Val Gln Val Cys
            900                 905                 910

Ser Thr Gln Val His Cys Ala Ala Glu Cys His Pro Pro Lys Asp His
        915                 920                 925

Ile Val Asn Tyr Pro Ala Ser His Thr Thr Leu Gly Val Gln Asp Ile
    930                 935                 940

Ser Ala Thr Ala Met Ser Trp Val Gln Lys Ile Thr Gly Gly Val Gly
945                 950                 955                 960

Leu Val Val Ala Val Ala Ala Leu Ile Leu Ile Val Val Leu Cys Val
                965                 970                 975

Ser Phe Ser Arg His
            980


<210> SEQ ID NO 22
<211> LENGTH: 981
<212> TYPE: PRT
<213> ORGANISM: Chikungunya virus

<400> SEQUENCE: 22

Leu Cys Leu Leu Ala Asn Thr Thr Phe Pro Cys Ser Gln Pro Pro Cys
1               5                   10                  15

Thr Pro Cys Cys Tyr Glu Lys Glu Pro Glu Ser Thr Leu Arg Met Leu
            20                  25                  30

Glu Asp Asn Val Met Arg Pro Gly Tyr Tyr Gln Leu Leu Lys Ala Ser
        35                  40                  45

Leu Thr Cys Ser Pro His Arg Gln Arg Arg Ser Thr Lys Asp Asn Phe
    50                  55                  60

Asn Val Tyr Lys Ala Thr Arg Pro Tyr Leu Ala His Cys Pro Asp Cys
65                  70                  75                  80

Gly Glu Gly His Ser Cys His Ser Pro Ile Ala Leu Glu Arg Ile Arg
                85                  90                  95

Asn Glu Ala Thr Asp Gly Thr Leu Lys Ile Gln Val Ser Leu Gln Ile
            100                 105                 110

Gly Ile Lys Thr Asp Asp Ser His Asp Trp Thr Lys Leu Arg Tyr Met
        115                 120                 125

Asp Ser His Thr Pro Ala Asp Ala Glu Arg Ala Gly Leu Leu Val Arg
    130                 135                 140

Thr Ser Ala Pro Cys Thr Ile Thr Gly Thr Met Gly His Phe Ile Leu
145                 150                 155                 160

Ala Arg Cys Pro Lys Gly Glu Thr Leu Thr Val Gly Phe Thr Asp Ser
                165                 170                 175

Arg Lys Ile Ser His Thr Cys Thr His Pro Phe His His Glu Pro Pro
            180                 185                 190

Val Ile Gly Arg Glu Arg Phe His Ser Arg Pro Gln His Gly Lys Glu
        195                 200                 205

Leu Pro Cys Ser Thr Tyr Val Gln Ser Thr Ala Ala Thr Ala Glu Glu
    210                 215                 220

Ile Glu Val His Met Pro Pro Asp Thr Pro Asp Arg Thr Leu Met Thr
225                 230                 235                 240

Gln Gln Ser Gly Asn Val Lys Ile Thr Val Asn Gly Gln Thr Val Arg
                245                 250                 255

Tyr Lys Cys Asn Cys Gly Gly Ser Asn Glu Gly Leu Thr Thr Thr Asp
```

-continued

```
            260                 265                 270

Lys Val Ile Asn Asn Cys Lys Ile Asp Gln Cys His Ala Ala Val Thr
        275                 280                 285

Asn His Lys Asn Trp Gln Tyr Asn Ser Pro Leu Val Pro Arg Asn Ala
    290                 295                 300

Glu Leu Gly Asp Arg Lys Gly Lys Ile His Ile Pro Phe Pro Leu Ala
305                 310                 315                 320

Asn Val Thr Cys Arg Val Pro Lys Ala Arg Asn Pro Thr Val Thr Tyr
                325                 330                 335

Gly Lys Asn Gln Val Thr Met Leu Leu Tyr Pro Asp His Pro Thr Leu
            340                 345                 350

Leu Ser Tyr Arg Asn Met Gly Gln Glu Pro Asn Tyr His Glu Glu Trp
        355                 360                 365

Val Thr His Lys Lys Glu Val Thr Leu Thr Val Pro Thr Glu Gly Leu
    370                 375                 380

Glu Val Thr Trp Gly Asn Asn Glu Pro Tyr Lys Tyr Trp Pro Gln Met
385                 390                 395                 400

Ser Thr Asn Gly Thr Ala His Gly His Pro His Glu Ile Ile Leu Tyr
                405                 410                 415

Tyr Tyr Glu Leu Tyr Pro Thr Met Thr Val Val Ile Val Ser Val Ala
            420                 425                 430

Ser Phe Val Leu Leu Ser Met Val Gly Thr Ala Val Gly Met Cys Val
        435                 440                 445

Cys Ala Arg Arg Arg Cys Ile Thr Pro Tyr Glu Leu Thr Pro Gly Ala
    450                 455                 460

Thr Val Pro Phe Leu Leu Ser Leu Leu Cys Cys Val Arg Thr Thr Lys
465                 470                 475                 480

Ala Ala Thr Tyr Tyr Glu Ala Ala Ala Tyr Leu Trp Asn Glu Gln Gln
                485                 490                 495

Pro Leu Phe Trp Leu Gln Ala Leu Ile Pro Leu Ala Ala Leu Ile Val
            500                 505                 510

Leu Cys Asn Cys Leu Lys Leu Leu Pro Cys Cys Cys Lys Thr Leu Ala
        515                 520                 525

Phe Leu Ala Val Met Ser Ile Gly Ala His Thr Val Ser Ala Tyr Glu
    530                 535                 540

His Val Thr Val Ile Pro Asn Thr Val Gly Val Pro Tyr Lys Thr Leu
545                 550                 555                 560

Val Asn Arg Pro Gly Tyr Ser Pro Met Val Leu Glu Met Glu Leu Gln
                565                 570                 575

Ser Val Thr Leu Glu Pro Thr Leu Ser Leu Asp Tyr Ile Thr Cys Glu
            580                 585                 590

Tyr Lys Thr Val Ile Pro Ser Pro Tyr Val Lys Cys Cys Gly Thr Ala
        595                 600                 605

Glu Cys Lys Asp Lys Ser Leu Pro Asp Tyr Ser Cys Lys Val Phe Thr
    610                 615                 620

Gly Val Tyr Pro Phe Met Trp Gly Gly Ala Tyr Cys Phe Cys Asp Ala
625                 630                 635                 640

Glu Asn Thr Gln Leu Ser Glu Ala His Val Glu Lys Ser Glu Ser Cys
                645                 650                 655

Lys Thr Glu Phe Ala Ser Ala Tyr Arg Ala His Thr Ala Ser Ala Ser
            660                 665                 670

Ala Lys Leu Arg Val Leu Tyr Gln Gly Asn Asn Ile Thr Val Ala Ala
        675                 680                 685
```

```
Tyr Ala Asn Gly Asp His Ala Val Thr Val Lys Asp Ala Lys Phe Val
    690                 695                 700

Val Gly Pro Met Ser Ser Ala Trp Thr Pro Phe Asp Asn Lys Ile Val
705                 710                 715                 720

Val Tyr Lys Gly Asp Val Tyr Asn Met Asp Tyr Pro Pro Phe Gly Ala
                725                 730                 735

Gly Arg Pro Gly Gln Phe Gly Asp Ile Gln Ser Arg Thr Pro Glu Ser
            740                 745                 750

Lys Asp Val Tyr Ala Asn Thr Gln Leu Val Leu Gln Arg Pro Ala Ala
        755                 760                 765

Gly Thr Val His Val Pro Tyr Ser Gln Ala Pro Ser Gly Phe Lys Tyr
    770                 775                 780

Trp Leu Lys Glu Arg Gly Ala Ser Leu Gln His Thr Ala Pro Phe Gly
785                 790                 795                 800

Cys Gln Ile Ala Thr Asn Pro Val Arg Ala Val Asn Cys Ala Val Gly
                805                 810                 815

Asn Ile Pro Ile Ser Ile Asp Ile Pro Asp Ala Ala Phe Thr Arg Val
            820                 825                 830

Val Asp Ala Pro Ser Val Thr Asp Met Ser Cys Glu Val Pro Ala Cys
        835                 840                 845

Thr His Ser Ser Asp Phe Gly Gly Val Ala Ile Ile Lys Tyr Thr Ala
    850                 855                 860

Ser Lys Lys Gly Lys Cys Ala Val His Ser Met Thr Asn Ala Val Thr
865                 870                 875                 880

Ile Arg Glu Ala Asp Val Glu Val Glu Gly Asn Ser Gln Leu Gln Ile
                885                 890                 895

Ser Phe Ser Thr Ala Leu Ala Ser Ala Glu Phe Arg Val Gln Val Cys
            900                 905                 910

Ser Thr Gln Val His Cys Ala Ala Ala Cys His Pro Pro Lys Asp His
        915                 920                 925

Ile Val Asn Tyr Pro Ala Ser His Thr Thr Leu Gly Val Gln Asp Ile
    930                 935                 940

Ser Thr Thr Ala Met Ser Trp Val Gln Lys Ile Thr Gly Gly Val Gly
945                 950                 955                 960

Leu Ile Val Ala Val Ala Ala Leu Ile Leu Ile Val Val Leu Cys Val
                965                 970                 975

Ser Phe Ser Arg His
            980


<210> SEQ ID NO 23
<211> LENGTH: 981
<212> TYPE: PRT
<213> ORGANISM: Chikungunya virus

<400> SEQUENCE: 23

Met Cys Leu Leu Ala Asn Thr Thr Phe Pro Cys Ser Gln Pro Pro Cys
1               5                   10                  15

Thr Pro Cys Cys Tyr Glu Lys Glu Pro Glu Lys Thr Leu Arg Met Leu
            20                  25                  30

Glu Asp Asn Val Met Ser Pro Gly Tyr Tyr Gln Leu Leu Gln Ala Ser
        35                  40                  45

Leu Thr Cys Ser Pro Arg Arg Gln Arg Arg Ser Ile Lys Asp Asn Phe
    50                  55                  60

Asn Val Tyr Lys Ala Thr Arg Pro Tyr Leu Ala His Cys Pro Asp Cys
```

-continued

```
65                  70                  75                  80

Gly Glu Gly His Ser Cys His Ser Pro Val Ala Leu Glu Arg Ile Arg
                85                  90                  95

Asn Glu Ala Thr Asp Gly Thr Leu Lys Ile Gln Val Ser Leu Gln Ile
            100                 105                 110

Gly Ile Lys Thr Asp Asp Ser His Asp Trp Thr Lys Leu Arg Tyr Met
        115                 120                 125

Asp Asn His Met Pro Ala Asp Ala Glu Arg Ala Gly Leu Phe Val Arg
    130                 135                 140

Thr Ser Ala Pro Cys Thr Ile Thr Gly Thr Met Gly His Phe Ile Leu
145                 150                 155                 160

Ala Arg Cys Pro Lys Gly Glu Thr Leu Thr Val Gly Phe Thr Asp Gly
                165                 170                 175

Arg Lys Ile Ser His Ser Cys Thr His Pro Phe His His Asp Pro Pro
            180                 185                 190

Val Ile Gly Arg Glu Lys Phe His Ser Arg Pro Gln His Gly Arg Glu
        195                 200                 205

Leu Pro Cys Ser Thr Tyr Ala Gln Ser Thr Ala Ala Thr Ala Glu Glu
    210                 215                 220

Ile Glu Val His Met Pro Pro Asp Thr Pro Asp Arg Thr Leu Met Ser
225                 230                 235                 240

Gln Gln Ser Gly Asn Val Lys Ile Thr Val Asn Ser Gln Thr Val Arg
                245                 250                 255

Tyr Lys Cys Asn Cys Gly Asp Ser Asn Glu Gly Leu Thr Thr Thr Asp
            260                 265                 270

Lys Val Ile Asn Asn Cys Lys Val Asp Gln Cys His Ala Ala Val Thr
        275                 280                 285

Asn His Lys Lys Trp Gln Tyr Asn Ser Pro Leu Val Pro Arg Asn Ala
    290                 295                 300

Glu Leu Gly Asp Arg Lys Gly Lys Val His Ile Pro Phe Pro Leu Ala
305                 310                 315                 320

Asn Val Thr Cys Arg Val Pro Lys Ala Arg Asn Pro Thr Val Thr Tyr
                325                 330                 335

Gly Lys Asn Gln Val Ile Met Leu Leu Tyr Pro Asp His Pro Thr Leu
            340                 345                 350

Leu Ser Tyr Arg Asn Met Gly Glu Glu Pro Asn Tyr Gln Glu Glu Trp
        355                 360                 365

Val Thr His Lys Lys Glu Ile Arg Leu Thr Val Pro Thr Glu Gly Leu
    370                 375                 380

Glu Val Thr Trp Gly Asn Asn Glu Pro Tyr Lys Tyr Trp Pro Gln Leu
385                 390                 395                 400

Ser Thr Asn Gly Thr Ala His Gly His Pro His Glu Ile Ile Leu Tyr
                405                 410                 415

Tyr Tyr Glu Leu Tyr Pro Thr Met Thr Val Val Val Val Ser Val Ala
            420                 425                 430

Ser Phe Val Leu Leu Ser Met Val Gly Val Ala Val Gly Met Cys Met
        435                 440                 445

Cys Ala Arg Arg Arg Cys Ile Thr Pro Tyr Glu Leu Thr Pro Gly Ala
    450                 455                 460

Thr Val Pro Phe Leu Leu Ser Leu Ile Cys Cys Ile Arg Thr Ala Lys
465                 470                 475                 480

Ala Ala Thr Tyr Gln Glu Ala Ala Val Tyr Leu Trp Asn Glu Gln Gln
                485                 490                 495
```

-continued

```
Pro Leu Phe Trp Leu Gln Ala Leu Ile Pro Leu Ala Ala Leu Ile Val
            500                 505                 510

Leu Cys Asn Cys Leu Arg Leu Leu Pro Cys Cys Cys Lys Thr Leu Thr
        515                 520                 525

Phe Leu Ala Val Leu Ser Val Gly Ala His Thr Val Ser Ala Tyr Glu
    530                 535                 540

His Val Thr Val Ile Pro Asn Thr Val Gly Val Pro Tyr Lys Thr Leu
545                 550                 555                 560

Val Asn Arg Pro Gly Tyr Ser Pro Met Val Leu Glu Met Glu Leu Leu
                565                 570                 575

Ser Val Thr Leu Glu Pro Thr Leu Ser Leu Asp Tyr Ile Thr Cys Glu
            580                 585                 590

Tyr Lys Thr Val Ile Pro Ser Pro Tyr Val Lys Cys Cys Gly Thr Ala
        595                 600                 605

Glu Cys Lys Asp Lys Ser Leu Pro Asp Tyr Ser Cys Lys Val Phe Thr
    610                 615                 620

Gly Val Tyr Pro Phe Met Trp Gly Gly Ala Tyr Cys Phe Cys Asp Thr
625                 630                 635                 640

Glu Asn Thr Gln Leu Ser Glu Ala His Val Glu Lys Ser Glu Ser Cys
                645                 650                 655

Lys Thr Glu Phe Ala Ser Ala Tyr Arg Ala His Thr Ala Ser Ala Ser
            660                 665                 670

Ala Lys Leu Arg Val Leu Tyr Gln Gly Asn Asn Val Thr Val Ser Ala
        675                 680                 685

Tyr Ala Asn Gly Asp His Ala Val Thr Val Lys Asp Ala Lys Phe Ile
    690                 695                 700

Val Gly Pro Met Ser Ser Ala Trp Thr Pro Phe Asp Asn Lys Ile Val
705                 710                 715                 720

Val Tyr Lys Gly Asp Val Tyr Asn Met Asp Tyr Pro Pro Phe Gly Ala
                725                 730                 735

Gly Arg Pro Gly Gln Phe Gly Asp Ile Gln Ser Arg Thr Pro Glu Ser
            740                 745                 750

Glu Asp Val Tyr Ala Asn Thr Gln Leu Val Leu Gln Arg Pro Ser Ala
        755                 760                 765

Gly Thr Val His Val Pro Tyr Ser Gln Ala Pro Ser Gly Phe Lys Tyr
    770                 775                 780

Trp Leu Lys Glu Arg Gly Ala Ser Leu Gln His Thr Ala Pro Phe Gly
785                 790                 795                 800

Cys Gln Ile Ala Thr Asn Pro Val Arg Ala Met Asn Cys Ala Val Gly
                805                 810                 815

Asn Met Pro Ile Ser Ile Asp Ile Pro Asp Ala Ala Phe Thr Arg Val
            820                 825                 830

Val Asp Ala Pro Ser Leu Thr Asp Met Ser Cys Glu Val Ser Ala Cys
        835                 840                 845

Thr His Ser Ser Asp Phe Gly Gly Val Ala Ile Ile Lys Tyr Ala Ala
    850                 855                 860

Ser Lys Lys Gly Lys Cys Ala Val His Ser Met Thr Asn Ala Val Thr
865                 870                 875                 880

Ile Arg Glu Ala Glu Ile Glu Val Glu Gly Asn Ser Gln Leu Gln Ile
                885                 890                 895

Ser Phe Ser Thr Ala Leu Ala Ser Ala Glu Phe Arg Val Gln Val Cys
            900                 905                 910
```

-continued

```
Ser Thr Gln Val His Cys Ala Ala Glu Cys His Pro Pro Lys Asp His
        915                 920                 925

Ile Val Asn Tyr Pro Ala Ser His Thr Thr Leu Gly Val Gln Asp Ile
    930                 935                 940

Ser Ala Thr Ala Met Ser Trp Val Gln Lys Ile Thr Gly Gly Val Gly
945                 950                 955                 960

Leu Val Val Ala Val Ala Ala Leu Ile Leu Ile Val Val Leu Cys Val
                965                 970                 975

Ser Phe Ser Arg His
            980
```

BROAD-SPECTRUM MONOCLONAL ANTIBODIES AGAINST CHIKUNGUNYA VIRUS E1 STRUCTURAL PROTEIN

TECHNICAL FIELD

The present invention relates to a new antibody against Chikungunya virus or an antigen-binding fragment of the antibody, and use of the same.

BACKGROUND ART

In Southeast Asia and elsewhere, epidemic diseases are transmitted by mosquitoes such as Aedes aegypti and Aedes albopictus. The epidemic diseases include dengue fever, Chikungunya fever, and Zika fever.

If the epidemic disease is suspected, it is necessary to determine which epidemic disease the patient has prior to treatment. For this reason, the causative virus test is performed.

SUMMARY OF INVENTION

Technical Problem

The inventors of the present invention have obtained CK47 antibody and CK119 antibody that bind to an E1 protein that constitutes the envelope sugar protein (hereinafter, also referred to as "Env protein") of Chikungunya virus (hereinafter, also referred to as "CHIKV") which is the pathogen of Chikungunya fever. However, CK47 antibody was bound strongly only to one genotype (ECSA) of three genotypes (ECSA (East/Central/South African), WA (West African), and Asian) of CHIKV. Furthermore, while CK119 antibody was bound to the three genotypes of CHIKV, it is strongly cross-reactive to Sindbis virus (SINV) of the same *Alphavirus* genus. Thus, there is a need for an antibody that binds to the three genotypes of CHIKV and does not bind to SINV.

With the foregoing in mind, it is an object of the present invention to provide a new antibody against three genotypes of CHIKV, namely ECSA type CHIKV, WA type CHIKV, and Asian type CHIKV or an antigen-binding fragment of the antibody.

Solution to Problem

In order to achieve the above object, the present invention provides an antibody against Chikungunya virus or an antigen-binding fragment of the antibody (hereinafter, also referred to as "antibody or the like"), including the following heavy chain variable region (1), (2), or (3) and the following light chain variable region (4).

(1) a heavy chain variable region including heavy chain complementarity determining regions (CDRH)1, CDRH2, and CDRH3:

CDRH1 is a polypeptide including the following amino acid sequence (H1-A),

CDRH2 is a polypeptide including the following amino acid sequence (H2-A), and

CDRH3 is a polypeptide including the following amino acid sequence (H3-A), wherein (H1-A) the following amino acid sequence (H1-A1), (H1-A2), or (H1-A3):

(H1-A1) an amino acid sequence of SEQ ID NO: 1 (GYTFTSYW), (H1-A2) an amino acid sequence having 80% or more identity with respect to the amino acid sequence of SEQ ID NO: 1, and (H1-A3) an amino acid sequence in which one or several amino acids are deleted, substituted, inserted and/or added in the amino acid sequence of SEQ ID NO: 1, (H2-A) the following amino acid sequence (H2-A1), (H2-A2), or (H2-A3):

(H2-A1) an amino acid sequence of SEQ ID NO: 2 (IYPGDGDTRYT), (H2-A2) an amino acid sequence having 80% or more identity with respect to the amino acid sequence of SEQ ID NO: 2, and (H2-A3) an amino acid sequence in which one or several amino acids are deleted, substituted, inserted and/or added in the amino acid sequence of SEQ ID NO: 2, (H3-A) the following amino acid sequence (H3-A1), (H3-A2), or (H3-A3):

(H3-A1) an amino acid sequence of SEQ ID NO: 3 (SYDPFDY), (H3-A2) an amino acid sequence having 80% or more identity with respect to the amino acid sequence of SEQ ID NO: 3, and (H3-A3) an amino acid sequence in which one or several amino acids are deleted, substituted, inserted and/or added in the amino acid sequence of SEQ ID NO: 3.

(2) a heavy chain variable region including CDRH1, CDRH2, and CDRH3:

CDRH1 is a polypeptide including the following amino acid sequence (H1-B),

CDRH2 is a polypeptide including the following amino acid sequence (H2-B), and

CDRH3 is a polypeptide including the following amino acid sequence (H3-B), wherein (H1-B) the following amino acid sequence (H1-B1), (H1-B2), or (H1-B3):

(H1-B1) an amino acid sequence of SEQ ID NO: 4 (GYAFSTSW), (H1-B2) an amino acid sequence having 80% or more identity with respect to the amino acid sequence of SEQ ID NO: 4, and (H1-B3) an amino acid sequence in which one or several amino acids are deleted, substituted, inserted and/or added in the amino acid sequence of SEQ ID NO: 4, (H2-B) the following amino acid sequence (H2-B1), (H2-B2), or (H2-B3):

(H2-B1) an amino acid sequence of SEQ ID NO: 5 (IYPGDGDT), (H2-B2) an amino acid sequence having 80% or more identity with respect to the amino acid sequence of SEQ ID NO: 5, and (H2-B3) an amino acid sequence in which one or several amino acids are deleted, substituted, inserted and/or added in the amino acid sequence of SEQ ID NO: 5, (H3-B) the following amino acid sequence (H3-B1), (H3-B2), or (H3-B3):

(H3-B1) an amino acid sequence of SEQ ID NO: 6 (SNDGYYVGY), (H3-B2) an amino acid sequence having 80% or more identity with respect to the amino acid sequence of SEQ ID NO: 6, and (H3-B3) an amino acid sequence in which one or several amino acids are deleted, substituted, inserted and/or added in the amino acid sequence of SEQ ID NO: 6.

(3) a heavy chain variable region including CDRH1, CDRH2, and CDRH3:

CDRH1 is a polypeptide including the following amino acid sequence (H1-C),

CDRH2 is a polypeptide including the following amino acid sequence (H2-C),

CDRH3 is a polypeptide including the following amino acid sequence (H3-C), wherein (H1-C) the following amino acid sequence (H1-C1), (H1-C2), or (H1-C3):

(H1-C1) an amino acid sequence of SEQ ID NO: 7 (GYTFTSYY), (H1-C2) an amino acid sequence having 80% or more identity with respect to the amino acid sequence of SEQ ID NO: 7, and (H1-C3) an amino acid sequence in which one or several amino acids are deleted, substituted, inserted and/or added in the amino acid sequence of SEQ ID NO: 7, (H2-C) the following amino acid sequence (H2-C1), (H2-C2), or (H2-C3):

(H2-C1) an amino acid sequence of SEQ ID NO: 8 (INPSNGGT), (H2-C2) an amino acid sequence having 80% or more identity with respect to the amino acid sequence of SEQ ID NO: 8, and (H2-C3) an amino acid sequence in which one or several amino acids are deleted, substituted, inserted and/or added in the amino acid sequence of SEQ ID NO: 8, (H3-C) the following amino acid sequence (H3-C1), (H3-C2), or (H3-C3):

(H3-C1) an amino acid sequence of SEQ ID NO: 9 (GYYGNPFFAY), (H3-C2) an amino acid sequence having 80% or more identity with respect to the amino acid sequence of SEQ ID NO: 9, and (H3-C3) an amino acid sequence in which one or several amino acids are deleted, substituted, inserted and/or added in the amino acid sequence of SEQ ID NO: 9.

(4) a light chain variable region including light chain complementarity determining regions (CDRL)1, CDRL2, and CDRL3:

CDRL1 is a polypeptide including the following amino acid sequence (L1-A),

CDRL2 is a polypeptide including the following amino acid sequence (L2-A),

CDRL3 is a polypeptide including the following amino acid sequence (L3-A), wherein (L1-A) the following amino acid sequence (L1-A1), (L1-A2), or (L1-A3):

(L1-A1) an amino acid sequence of SEQ ID NO: 10 (ENVVTY), (L1-A2) an amino acid sequence having 80% or more identity with respect to the amino acid sequence of SEQ ID NO: 10, and (L1-A3) an amino acid sequence in which one or several amino acids are deleted, substituted, inserted and/or added in the amino acid sequence of SEQ ID NO: 10, (L2-A) the following amino acid sequence (L2-A1), (L2-A2), or (L2-A3):

(L2-A1) an amino acid sequence of SEQ ID NO: 11 (GAS), (L2-A2) an amino acid sequence having 80% or more identity with respect to the amino acid sequence of SEQ ID NO: 11, and (L2-A3) an amino acid sequence in which one or several amino acids are deleted, substituted, inserted and/or added in the amino acid sequence of SEQ ID NO: 11, (L3-A) the following amino acid sequence (L3-A1), (L3-A2), or (L3-A3):

(L3-A1) an amino acid sequence of SEQ ID NO: 12 (GQGYSYPYT), (L3-A2) an amino acid sequence having 80% or more identity with respect to the amino acid sequence of SEQ ID NO: 12, and (L3-A3) an amino acid sequence in which one or several amino acids are deleted, substituted, inserted and/or added in the amino acid sequence of SEQ ID NO: 12.

The present invention also provides an antibody against Chikungunya virus or an antigen-binding fragment of the antibody, including the following heavy chain variable region (1), (2), or (3) and the following light chain variable region (4).

(1) a heavy chain variable region including a polypeptide consisting of the following amino acid sequence (H-A):

(H-A) the following amino acid sequence (H-A1), (H-A2), or (H-A3):

(H-A1) an amino acid sequence of SEQ ID NO: 13, (H-A2) an amino acid sequence having 80% or more identity with respect to the amino acid sequence of SEQ ID NO: 13, and (H-A3) an amino acid sequence in which one or several amino acids are deleted, substituted, inserted and/or added in the amino acid sequence of SEQ ID NO: 13.

(2) a heavy chain variable region including a polypeptide consisting of the following amino acid sequence (H-B):

(H-B) the following amino acid sequence (H-B1), (H-B2), or (H-B3):

(H-B1) an amino acid sequence of SEQ ID NO: 14, (H-B2) an amino acid sequence having 80% or more identity with respect to the amino acid sequence of SEQ ID NO: 14, and (H-B3) an amino acid sequence in which one or several amino acids are deleted, substituted, inserted and/or added in the amino acid sequence of SEQ ID NO: 14.

(3) a heavy chain variable region including a polypeptide consisting of the following amino acid sequence (H-C):

(H-C) the following amino acid sequence (H-C1), (H-C2), or (H-C3):

(H-C1) an amino acid sequence of SEQ ID NO: 15, (H-C2) an amino acid sequence having 80% or more identity with respect to the amino acid sequence of SEQ ID NO: 15, and (H-C3) an amino acid sequence in which one or several amino acids are deleted, substituted, inserted and/or added in the amino acid sequence of SEQ ID NO: 15.

(4) a light chain variable region including a polypeptide consisting of the following amino acid sequence (L-A):

(L-A) the following amino acid sequence (L-A1), (L-A2), or (L-A3):

(L-A1) an amino acid sequence of SEQ ID NO: 16, (L-A2) an amino acid sequence having 80% or more identity with respect to the amino acid sequence of SEQ ID NO: 16, and (L-A3) an amino acid sequence in which one or several amino acids are deleted, substituted, inserted and/or added in the amino acid sequence of SEQ ID NO: 16.

The present invention also provides an antibody against Chikungunya virus or an antigen-binding fragment of the antibody, including the following heavy chain (1), (2), or (3) and the following light chain (4).

(1) a heavy chain including a polypeptide consisting of the following amino acid sequence (HA):

(HA) the following amino acid sequence (HA1), (HA2), or (HA3):

(HA1) an amino acid sequence of SEQ ID NO: 17, (HA2) an amino acid sequence having 80% or more identity with respect to the amino acid sequence of SEQ ID NO: 17, and (HA3) an amino acid sequence in which one or several amino acids are deleted, substituted, inserted and/or added in the amino acid sequence of SEQ ID NO: 17.

(2) a heavy chain including a polypeptide consisting of the following amino acid sequence (HB):

(HB) the following amino acid sequence (HB1), (HB2), or (HB3):

(HB1) an amino acid sequence of SEQ ID NO: 18, (HB2) an amino acid sequence having 80% or more identity with respect to the amino acid sequence of SEQ ID NO: 18, and (HB3) an amino acid sequence in which one or several amino acids are deleted, substituted, inserted and/or added in the amino acid sequence of SEQ ID NO: 18.

(3) a heavy chain including a polypeptide consisting of the following amino acid sequence (HC):

(HC) the following amino acid sequence (HC1), (HC2), or (HC3):

(HC1) an amino acid sequence of SEQ ID NO: 19, (HC2) an amino acid sequence having 80% or more identity with respect to the amino acid sequence of SEQ ID NO: 19, and (HC3) an amino acid sequence in which one or several amino acids are deleted, substituted, inserted and/or added in the amino acid sequence of SEQ ID NO: 19.

(4) a light chain including a polypeptide consisting of the following amino acid sequence (LA):

(LA) the following amino acid sequence (LA1), (LA2), or (LA3):

(LA1) an amino acid sequence of SEQ ID NO: 20, (LA2) an amino acid sequence having 80% or more identity with respect to the amino acid sequence of SEQ ID NO: 20, and (LA3) an amino acid sequence in which one or several amino acids are deleted, substituted, inserted and/or added in the amino acid sequence of SEQ ID NO: 20.

The present invention also provides a detection kit for Chikungunya virus (hereinafter, also referred to as a "detection kit"), including: the antibody or the antigen-binding fragment of the antibody of the present invention.

The present invention also provides a method for detecting Chikungunya virus (hereinafter, also referred to as a "detection method"), including: a detection step of bringing a sample into contact with the antibody or the antigen-binding fragment of the antibody of the present invention to bind Chikungunya virus in the sample to the antibody or the antigen-binding fragment of the antibody, thereby detecting Chikungunya virus in the sample.

Advantageous Effects of Invention

According to the present invention, a new antibody that binds to three genotypes of CHIKV, namely ECSA type CHIKV, WA type CHIKV, and Asian type CHIKV can be provided. Thus, according to the antibody or the like of the present invention, for example, CHIKV can be detected regardless of the genotype, and therefore, it can be suitably used for a detection kit for CHIKV.

DESCRIPTION OF EMBODIMENTS

Figures 1A, 1B, 1C:
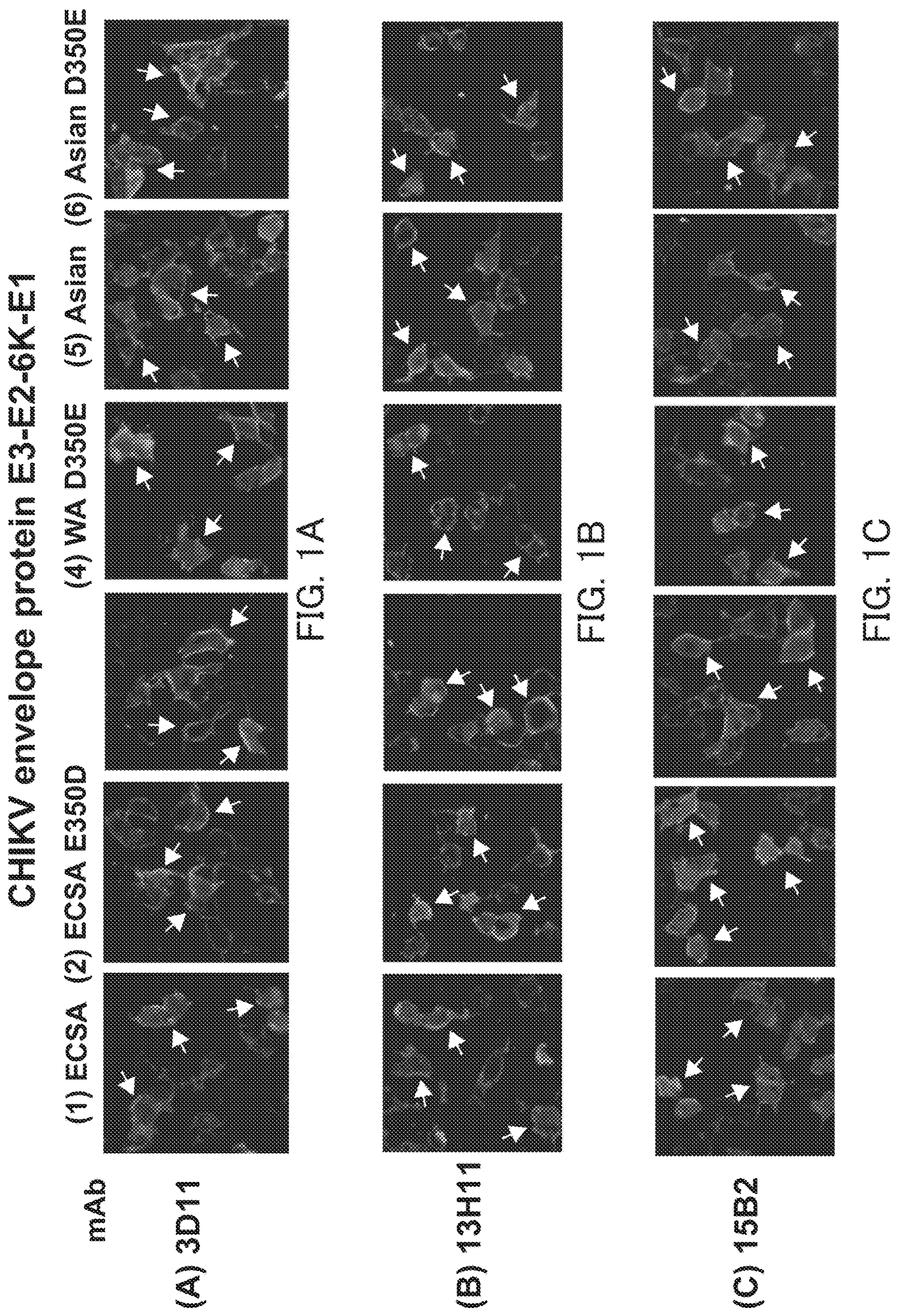
FIGS. 1A to 1C show photographs showing the staining results of cells expressing the envelope protein in Example 2.

Antibody or Antigen-Binding Fragment of the Antibody

As described above, the antibody against Chikungunya virus or the antigen-binding fragment of the antibody of the present invention includes the heavy chain variable region or heavy chain (1), (2), or (3) and the light chain variable region or light chain (4). The antibody or the like of the present invention is characterized in that it includes the heavy chain variable region or the heavy chain (1), (2), or (3) and the light chain variable region or the light chain (4), and other configurations and conditions are not particularly limited. The antibody or the like of the present invention binds to ECSA type CHIKV, WA type CHIKV, and Asian type CHIKV.

The antibody or the like of the present invention does not bind to, for example, Sindbis virus. Therefore, the antibody or the like of the present invention can be suitably used, for example, in a detection kit or the like for CHIKV to be described below.

In the present invention, "Chikungunya virus" refers to Chikungunya virus belonging to the genus *Alphavirus* of the family Togaviridae.

In the present invention, "Sindbis virus" refers to Sindbis virus belonging to the genus *Alphavirus* of the family Togaviridae.

The antibody or the like of the present invention binds to ECSA type CHIKV, WA type CHIKV, and Asian type CHIKV as described above. The ECSA type CHIKV, the WA type CHIKV, and the Asian type CHIKV can be classified with reference to the Reference 1 below, for example. More specifically, the antibody or the like of the present invention binds to an Env protein of ECSA type CHIKV, an Env protein of WA type CHIKV, and an Env protein of Asian type CHIKV, for example. The Env protein refers to an envelope protein of CHIKV, for example. The Env protein is also referred to as a E3-E2-6K-E1 protein because it is composed of a 6K-E1 protein, an E2 protein, and an E3 protein, for example. The amino acid sequence of the Env protein of CHIKV can be referred to, for example, information registered in an existing data base. As a specific example, an Env protein derived from ECSA type CHIKV includes, for example, the following amino acid sequence (SEQ ID NO: 21) from positions 268 to 1247 in the amino acid sequence registered under the NCBI Accession NO.: BAP74220.1. An Env protein derived from WA type CHIKV includes, for example, the following amino acid sequence (SEQ ID NO: 22) from positions 268 to 1247 in the amino acid sequence registered under the NCBI Accession NO.: AAU43881.1. An Env protein derived from Asian type CHIKV includes, for example, the following amino acid sequence (SEQ ID NO: 23) from positions 268 to 1247 in the amino acid sequence registered under the NCBI Accession NO.: ADG95938.1.

Reference 1: Aekkachai Tuekprakhon et. al., "Variation at position 350 in the Chikungunya virus 6K-E1 protein determines the sensitivity of detection in a rapid E1-antigen test", Scientific Report, vol. 8, Article Number:1094, 2018

```
Env protein derived from ECSA type CHIKV
                                    (SEQ ID NO: 21)
MCLLANTTFPCSQPPCTPCCYEKEPEETLRMLEDNVMRPGYYQLLQASL

TCSPHRQRRSTKDNFNVYKATRPYLAHCPDCGEGHSCHSPVALERIRNE

ATDGTLKIQVSLQIGIKTDDSHDWTKLRYMDNHMPADAERAGLFVRTSA

PCTITGTMGHFILARCPKGETLTVGFTDSRKISHSCTHPFHHDPPVIGR

EKFHSRPQHGKELPCSTYVQSTAATTEEIEVHMPPDTPDRTLMSQQSGN

VKITVNGQTVRYKCNCGGSNEGLTTTDKVINNCKVDQCHAAVTNHKKWQ

YNSPLVPRNAELGDRQGKIHIPFPLANVTCRVPKARNPTVTYGKNQVIM

LLYPDHPTLLSYRNMGEEPNYQEEWVMHKKEVVLTVPTEGLEVTWGNNE
```

-continued

PYKYWPQLSTNGTAHGHPHEIILYYYELYPTMTVVVVSVATFILLSMVG

MAAGMCMCARRRCITPYELTPGATVPFLLSLICCIRTAKAATYQEAAIY

LWNEQQPLFWLQALIPLAALIVLCNCLRLLPCCCKTLAFLAVMSVGAHT

VSAYEHVTVIPNTVGVPYKTLVNRPGYSPMVLEMELLSVTLEPTLSLDY

ITCEYKTVIPSPYVKCCGTAECKDKNLPDYSCKVFTGVYPFMWGGAYCF

CDAENTQLSEAHVEKSESCKTEFASAYRAHTASASAKLRVLYQGNNITV

TAYANGDHAVTVKDAKFIVGPMSSAWTPFDNKIVVYKGDVYNMDYPPFG

AGRPGQFGDIQSRTPESKDVYANTQLVLQRPAVGTVHVPYSQAPSGFKY

WLKERGASLQHTAPFGCQIATNPVRAVNCAVGNMPISIDIPEAAFTRVV

DAPSLTDMSCEVPACTHSSDFGGVAIIKYAASKKGKCAVHSMTNAVTIR

EAEIEVEGNSQLQISFSTALASAEFRVQVCSTQVHCAAECHPPKDHIVN

YPASHTTLGVQDISATAMSWVQKITGGVGLVVAVAALILIVVLCVSFSR

H

Env protein derived from WA type CHIKV (SEQ ID NO: 22)

LCLLANTTFPCSQPPCTPCCYEKEPESTLRMLEDNVMRPGYYQLLKASL

TCSPHRQRRSTKDNFNVYKATRPYLAHCPDCGEGHSCHSPIALERIRNE

ATDGTLKIQVSLQIGIKTDDSHDWTKLRYMDSHTPADAERAGLLVRTSA

PCTITGTMGHFILARCPKGETLTVGFTDSRKISHTCTHPFHHEPPVIGR

ERFHSRPQHGKELPCSTYVQSTAATAEEIEVHMPPDTPDRTLMTQQSGN

VKITVNGQTVRYKCNCGGSNEGLTTTDKVINNCKIDQCHAAVTNHKNWQ

YNSPLVPRNAELGDRKGKIHIPFPLANVTCRVPKARNPTVTYGKNQVTM

LLYPDHPTLLSYRNMGQEPNYHEEWVTHKKEVTLTVPTEGLEVTWGNNE

PYKYWPQMSTNGTAHGHPHEIILYYYELYPTMTVVIVSVASFVLLSMVG

TAVGMCVCARRRCITPYELTPGATVPFLLSLLCCVRTTKAATYYEAAAY

LWNEQQPLFWLQALIPLAALIVLCNCLKLLPCCCKTLAFLAVMSIGAHT

VSAYEHVTVIPNTVGVPYKTLVNRPGYSPMVLEMELQSVTLEPTLSLDY

ITCEYKTVIPSPYVKCCGTAECKDKSLPDYSCKVFTGVYPFMWGGAYCF

CDAENTQLSEAHVEKSESCKTEFASAYRAHTASASAKLRVLYQGNNITV

AAYANGDHAVTVKDAKFVVGPMSSAWTPFDNKIVVYKGDVYNMDYPPFG

AGRPGQFGDIQSRTPESKDVYANTQLVLQRPAAGTVHVPYSQAPSGFKY

WLKERGASLQHTAPFGCQIATNPVRAVNCAVGNIPISIDIPDAAFTRVV

DAPSVTDMSCEVPACTHSSDFGGVAIIKYTASKKGKCAVHSMTNAVTIR

EADVEVEGNSQLQISFSTALASAEFRVQVCSTQVHCAAACHPPKDHIVN

YPASHTTLGVQDISTTAMSWVQKITGGVGLIVAVAALILIVVLCVSFSR

H

Env protein from Asian type CHIKV (SEQ ID NO: 23)

MCLLANTTFPCSQPPCTPCCYEKEPEKTLRMLEDNVMSPGYYQLLQASL

TCSPRRQRRSIKDNFNVYKATRPYLAHCPDCGEGHSCHSPVALERIRNE

ATDGTLKIQVSLQIGIKTDDSHDWTKLRYMDNHMPADAERAGLFVRTSA

PCTITGTMGHFILARCPKGETLTVGFTDGRKISHSCTHPFHHDPPVIGR

-continued

EKFHSRPQHGRELPCSTYAQSTAATAEEIEVHMPPDTPDRTLMSQQSGN

VKITVNSQTVRYKCNCGDSNEGLTTTDKVINNCKVDQCHAAVTNHKKWQ

YNSPLVPRNAELGDRKGKVHIPFPLANVTCRVPKARNPTVTYGKNQVIM

LLYPDHPTLLSYRNMGEEPNYQEEWVTHKKEIRLTVPTEGLEVTWGNNE

PYKYWPQLSTNGTAHGHPHEIILYYYELYPTMTVVVVSVASFVLLSMVG

VAVGMCMCARRRCITPYELTPGATVPFLLSLICCIRTAKAATYQEAAVY

LWNEQQPLFWLQALIPLAALIVLCNCLRLLPCCCKTLTFLAVLSVGAHT

VSAYEHVTVIPNTVGVPYKTLVNRPGYSPMVLEMELLSVTLEPTLSLDY

ITCEYKTVIPSPYVKCCGTAECKDKSLPDYSCKVFTGVYPFMWGGAYCF

CDTENTQLSEAHVEKSESCKTEFASAYRAHTASASAKLRVLYQGNNVTV

SAYANGDHAVTVKDAKFIVGPMSSAWTPFDNKIVVYKGDVYNMDYPPFG

AGRPGQFGDIQSRTPESEDVYANTQLVLQRPSAGTVHVPYSQAPSGFKY

WLKERGASLQHTAPFGCQIATNPVRAIVINCAVGNMPISIDIPDAAFTR

VVDAPSLTDMSCEVSACTHSSDFGGVAIIKYAASKKGKCAVHSMTNAVT

IREAEIEVEGNSQLQISFSTALASAEFRVQVCSTQVHCAAECHPPKDHI

VNYPASHTTLGVQDISATAMSWVQKITGGVGLVVAVAALILIVVLCVSF

SRH

The antibody or the like of the present invention includes, for example, an antibody that binds to a peptide fragment of the Env protein, in addition to an antibody that binds to CHIKV, more specifically, a protein consisting of the full-length amino acid sequence of the Env protein. The Env protein includes, for example, a mutant Env protein (E350D) in which the amino acid (glutamic acid (E) underlined in SEQ ID NO: 21) corresponding to the amino acid at position 826 (position 284 of the E1 protein and position 350 of 6K-E1 protein) in the amino acid sequence of SEQ ID NO: 21 is substituted with an aspartic acid (D). The Env protein includes, for example, a mutant Env protein (D350E) in which the amino acid (aspartic acid (D) underlined in SEQ ID NO: 22 or 23) corresponding to the amino acid at position 826 (position 284 of the E1 protein and position 350 of 6K-E1 protein) in the amino acid sequence of SEQ ID NO: 22 or 23 is substituted with a glutamic acid (E). Hereinafter, for example, the Env protein includes, in addition to an Env protein consisting of the full-length amino acid sequence, a mutant Env protein (E350D), and a mutant Env protein (D350E), the meaning of the peptide fragments of these Env proteins, unless otherwise indicated. The CK47 antibody particularly weakly binds to the mutant Env protein (E350D), the Env protein derived from WA type CHIKV, and Env protein derived from Asian type CHIKV. According to the antibody or the like of the present invention, for example, the mutant Env protein (E350D), the Env protein derived from WA type CHIKV, and the Env protein derived from Asian type CHIKV can also be detected.

The present invention may be, for example, a so-called "antibody" in which the molecular structure is an immunoglobulin, or an antigen-binding fragment of the antibody. The antibody or the like of the present invention may have the heavy chain variable region and the light chain variable region. When the present invention is an antibody, for example, its immunoglobulin class and isotype are not particularly limited. Examples of the immunoglobulin class include IgG, IgM, IgA, IgD, and IgE. Examples of the IgG include IgG1, IgG2, IgG3, and IgG4.

Examples of the antibody include monoclonal antibodies, polyclonal antibodies, recombinant antibodies, human (e.g., fully human) antibodies, humanized antibodies, chimeric antibodies, and multispecific antibodies.

The "antigen-binding fragment" in the present invention refers to a part of the antibody, e.g., a partial fragment which recognizes (binds to) the Chikungunya virus. Examples of the antigen-binding fragment include Fab, Fab', $F(ab')_2$, variable region fragments (Fv), disulfide bond Fv, single-chain Fv (scFv), bispecific antibodies, and polymers thereof.

The antibody or the like of the present invention may have, for example, a constant region in addition to the heavy chain variable region and the light chain variable region described above, and the constant region is, for example, a human constant region or a mouse constant region. In the case of the antibody (immunoglobulin), the constant region of a heavy chain includes regions CH1, CH2, and CH3, for example, and the constant region of a light chain includes a region CL, for example. When the antibody or the like of the present invention includes the constant region, for example, the heavy chain variable region is bound to at least one of CH1, CH2, and CH3, the light chain variable region is bound to the CL, and the heavy chain variable region is directly bound to the CH1, for example.

Generally, the heavy chain and the light chain of an antibody molecule each include three complementarity determining regions (CDRs). The CDR is also referred to as a hypervariable domain. The CDR is a region in which the primary structure is highly variable among the variable regions of the heavy chain and the light chain, and is usually separated in three sites on the primary structure. In the present invention, three sites of CDR in the heavy chain are denoted as heavy chain CDR1 (CDRH1), heavy chain CDR2 (CDRH2), and heavy chain CDR3 (CDRH3) from the amino terminal side in the amino acid sequence of the heavy chain, and three sites of CDR in the light chain are denoted as light chain CDR1 (CDRL1), light chain CDR2 (CDRL2), and light chain CDR3 (CDRL3) from the amino terminal side in the amino acid sequence of the light chain. These sites are conformationally close to each other and determine the specificity for the antigen to be bound.

Hereinafter, as to the antibody or the like of the present invention, the combination of the heavy chain variable region or heavy chain and the light chain variable region or light chain will be described. Regarding the description of the heavy chain variable region in each combination and the description of the heavy chain in each combination, reference can be made to one another. Regarding the description of the light chain variable region in each combination and description of the light chain in each combination, reference can be made to one another.

In the antibody or the like of the present invention, the combination of the heavy chain variable region or the heavy chain and the light chain variable region or the light chain is the combination of (1) and (4), the combination of (2) and (4), or the combination of (3) and (4).

Combination of (1) and (4)

The antibody or the like of the combination of (1) and (4) is also referred to as an antibody 3D11 group, for example. In the combination of (1) and (4), the heavy chain variable region (1) includes heavy chain complementarity determining regions (CDRH)1, CDRH2, and CDRH3, wherein CDRH1 is a polypeptide including the following amino acid sequence (H1-A), CDRH2 is a polypeptide including the following amino acid sequence (H2-A), and CDRH3 is a polypeptide including the following amino acid sequence (H3-A). Further, the light chain variable region (4) includes a light chain complementarity determining region (CDRL) 1, CDRL2, and CDRL3, wherein CDRL1 is a polypeptide including the following amino acid sequence (L1-A), CDRL2 is a polypeptide including the following amino acid sequence (L2-A), and CDRL3 is a polypeptide including the following amino acid sequence (L3-A).

(H1-A) the following amino acid sequence (H1-A1), (H1-A2), or (H1-A3):

(H1-A1) an amino acid sequence of SEQ ID NO: 1 (GYTFTSYW), (H1-A2) an amino acid sequence having 80% or more identity with respect to the amino acid sequence of SEQ ID NO: 1, and (H1-A3) an amino acid sequence in which one or several amino acids are deleted, substituted, and inserted and/or added in the amino acid sequence of SEQ ID NO: 1.

(H2-A) the following amino acid sequence (H2-A1), (H2-A2), or (H2-A3):

(H2-A1) an amino acid sequence of SEQ ID NO: 2 (IYPGDGDTRYT), (H2-A2) an amino acid sequence having 80% or more identity with respect to the amino acid sequence of SEQ ID NO: 2, and (H2-A3) an amino acid sequence in which one or several amino acids are deleted, substituted, inserted and/or added in the amino acid sequence of SEQ ID NO: 2.

(H3-A) the following amino acid sequence (H3-A1), (H3-A2), or (H3-A3):

(H3-A1) an amino acid sequence of SEQ ID NO: 3 (SYDPFDY), (H3-A2) an amino acid sequence having 80% or more identity with respect to the amino acid sequence of SEQ ID NO: 3, and (H3-A3) an amino acid sequence in which one or several amino acids are deleted, substituted, inserted and/or added in the amino acid sequence of SEQ ID NO: 3.

(L1-A) the following amino acid sequence (L1-A1), (L1-A2), or (L1-A3):

(L1-A1) an amino acid sequence of SEQ ID NO: 10 (ENVVTY), (L1-A2) an amino acid sequence having 80% or more identity with respect to the amino acid sequence of SEQ ID NO: 10, and (L1-A3) an amino acid sequence in which one or several amino acids are deleted, substituted, inserted and/or added in the amino acid sequence of SEQ ID NO: 10.

(L2-A) the following amino acid sequence (L2-A1), (L2-A2), or (L2-A3):

(L2-A1) an amino acid sequence of SEQ ID NO: 11 (GAS), (L2-A2) an amino acid sequence having 80% or more identity with respect to the amino acid sequence of SEQ ID NO: 11, and (L2-A3) an amino acid sequence in which one or several amino acids are deleted, substituted, inserted and/or added in the amino acid sequence of SEQ ID NO: 11.

(L3-A) the following amino acid sequence (L3-A1), (L3-A2), or (L3-A3):

(L3-A1) an amino acid sequence of SEQ ID NO: 12 (GQGYSYPYT), (L3-A2) an amino acid sequence having 80% or more identity with respect to the amino acid sequence of SEQ ID NO: 12, and (L3-A3) an amino acid sequence in which one or several amino acids are deleted, substituted, inserted and/or added in the amino acid sequence of SEQ ID NO: 12.

In each CDR, the "identity" is, for example, a degree of identity when the sequences to be compared are appropriately aligned, and means a rate of occurrence (%) of an accurate match of amino acids between the sequences. The "identity" is 80% or more, 85% or more, 90% or more, 95% or more, 96% or more, 97% or more, 98% or more, or 99% or more. The identity can be calculated, for example, by default parameters using analysis software such as BLAST, FASTA, and the like (hereinafter, the same applies).

In each CDR, "one or several" relating to substitution or the like is, for example, 1 to 5, 1 to 4, 1 to 3, 1 or 2, or 1.

The substitution of the amino acid may be, for example, a conservative substitution (hereinafter, the same applies). The conservative substitution means substituting one or several amino acids with other amino acids and/or amino acid derivatives so as not to substantially alter the function of the protein. It is preferable that the properties and/or functions of "an amino acid that substitutes an amino acid" and "an amino acid to be substituted with an amino acid" be similar to each other, for example. Specifically, it is preferable that, for example, a hydrophobic and hydrophilic indicator (hydropathy), a chemical property such as polarity or charge, or a physical property such as a secondary structure of "an amino acid that substitutes an amino acid" and "an amino acid to be substituted with an amino acid" be similar to each other. Amino acids or amino acid derivatives having similar properties and/or functions are known in the art, for example. Specific examples of the nonpolar amino acid (hydrophobic amino acid) include alanine, valine, isoleucine, leucine, proline, tryptophan, phenylalanine, and methionine. Specific examples of the polar amino acid (neutral amino acid) include glycine, serine, threonine, tyrosine, glutamine, asparagine, and cysteine. Specific examples of the amino acid (basic amino acid) having a positive charge include arginine, histidine, and lysine. Specific examples of the amino acid (acidic amino acid) having a negative charge include an aspartic acid and a glutamic acid.

In the combination of (1) and (4), the heavy chain variable region (1) includes a polypeptide consisting of the following amino acid sequence (H-A), for example. Further, the light chain variable region (4) includes a polypeptide consisting of the following amino acid sequence (L-A), for example.

(H-A) the following amino acid sequence (H-A1), (H-A2), or (H-A3):

(H-A1) an amino acid sequence of SEQ ID NO: 13,

```
SEQ ID NO: 3:
QVQLQQSGAELARPGASVKLSCKASGYTFTSYWMQWVKQRPGQGLEWIG
AIYPGDGDTRYTQKFKGKATLTADKSSSTAYMQLSSLASEDSAVYYCAR
SYDPFDYWGQGTTLTVSS,
```

(H-A2) an amino acid sequence having 80% or more identity with respect to the amino acid sequence of SEQ ID NO: 13, and (H-A3) an amino acid sequence in which one or several amino acids are deleted, substituted, inserted and/or added in the amino acid sequence of SEQ ID NO: 13.

(L-A) the following amino acid sequence (L-A1), (L-A2), or (L-A3):

(L-A1) an amino acid sequence of SEQ ID NO: 16,

```
SEQ ID NO: 16:
NIVMTQSPKSMSMSVGERVTLTCKASENVVTYVSWYQQKPEQSPKLLIY
GASNRYTGVPDRFTGSGSATDFTLTISSVQAEDLADYHCGQGYSYPYTF
GGGTKLEI,
```

(L-A2) an amino acid sequence having 80% or more identity with respect to the amino acid sequence of SEQ ID NO: 16, and (L-A3) an amino acid sequence in which one or several amino acids are deleted, substituted, inserted and/or added in the amino acid sequence of SEQ ID NO: 16.

The amino acid sequence (H-A1) is a sequence including the amino acid sequences (H1-A1) of CDRH1, (H2-A1) of CDRH2, and (H3-A1) of CDRH3, for example. The amino acid sequence (H-A2) may be an amino acid sequence including the amino acid sequences (H1-A1) of CDRH1, (H2-A1) of CDRH2, and (H3-A1) of CDRH3 and having 80% or more identity with respect to the amino acid sequence of SEQ ID NO: 13, for example. The amino acid sequence (H-A3) may be an amino acid sequence including the amino acid sequences (H1-A1) of CDRH1, (H2-A1) of CDRH, and (H3-A1) of CDRH3 and in which one or several amino acids are deleted, substituted, inserted, and/or added in the amino acid sequence of SEQ ID NO: 13, for example.

The amino acid sequence (L-A1) is a sequence including the amino acid sequences (L1-A1) of CDRL1, (L2-A1) of CDRL2, and (L3-A1) of CDRL3, for example. The amino acid sequence (L-A2) may be an amino acid sequence including the amino acid sequences (L1-A1) of CDRL1, (L2-A1) of CDRL2, and (L3-A1) of CDRL3 and having 80% or more identity with respect to the amino acid sequence of SEQ ID NO: 16, for example. The amino acid sequence (L-A3) may be an amino acid sequence including the amino acid sequences (L1-A1) of CDRL1, (L2-A1) of CDRL2, and (L3-A1) of CDRL3 and in which one or several amino acids are deleted, substituted, inserted, and/or added in the amino acid sequence of SEQ ID NO: 16, for example.

In the antibody of the present invention, for example, the heavy chain variable region is the (H-A1) and the light chain variable region is the (L-A1). The antibody of this combination is hereinafter also referred to as an "antibody 3D11".

In the polypeptide of the heavy chain variable region and the polypeptide of the light chain variable region, the "identity" is, for example, 80% or more, 85% or more, 90% or more, 95% or more, 96% or more, 97% or more, 98% or more, or 99% or more, respectively.

In the polypeptide of the heavy chain variable region and the polypeptide of the light chain variable region, "one or several" relating to substitution or the like is, for example, 1 to 20, 1 to 15, 1 to 10, 1 to 9, 1 to 8, 1 to 7, 1 to 6, 1 to 5, 1 to 4, 1 to 3, 1 or 2, or 1, respectively.

In the combination of (1) and (4), the heavy chain (1) includes a polypeptide consisting of the following amino acid sequence (HA), for example. Further, the light chain (4) includes a polypeptide consisting of the following amino acid sequence (LA), for example.

(1) a heavy chain including a polypeptide consisting of the following amino acid sequence (HA):

(HA) the following amino acid sequence (HA1), (HA2), or (HA3):

(HA1) an amino acid sequence of SEQ ID NO: 17, (HA2) an amino acid sequence having 80% or more identity with respect to the amino acid sequence of SEQ ID NO: 17, and (HA3) an amino acid sequence in which one or several amino acids are deleted, substituted, inserted and/or added in the amino acid sequence of SEQ ID NO: 17.

(4) a light chain including a polypeptide consisting of the following amino acid sequence (LA):

(LA) the following amino acid sequence (LA1), (LA2), or (LA3):

(LA1) an amino acid sequence of SEQ ID NO: 20, (LA2) an amino acid sequence having 80% or more identity with respect to the amino acid sequence of SEQ ID NO: 20, and (LA3) an amino acid sequence in which one or several amino acids are deleted, substituted, inserted and/or added in the amino acid sequence of SEQ ID NO: 20.

The amino acid sequence (HA1) is a sequence including the amino acid sequences (H1-A1) of CDRH1, (H2-A1) of CDRH2, and (H3-A1) of CDRH3, and/or a sequence including the amino acid sequence (H-A1). The amino acid sequence (HA2) may be an amino acid sequence including the amino acid sequences (H1-A1) of CDRH1, (H2-A1) of CDRH2, and (H3-A1) of CDRH3 and having 80% or more identity with respect to the amino acid sequence of SEQ ID NO: 17, for example. The amino acid sequence (HA2) may be an amino acid sequence including the amino acid sequence (H-A1) and having 80% or more identity with respect to the amino acid sequence of SEQ ID NO: 17, for example. The amino acid sequence (HA3) may be an amino acid sequence including the amino acid sequences (H1-A1) of CDRH1, (H2-A1) of CDRH2, and (H3-A1) of CDRH3 and in which one or several amino acids are deleted, substituted, inserted, and/or added in the amino acid sequence of SEQ ID NO: 17, for example. The amino acid sequence (HA3) may be an amino acid sequence including the amino acid sequence (H-A1) and in which one or several amino acids are deleted, substituted, inserted and/or added in the amino acid sequence of SEQ ID NO: 17, for example.

The amino acid sequence (LA1) is a sequence including the amino acid sequences (L1-A1) of CDRL1, (L2-A1) of CDRL2, and (L3-A1) of CDRL3, and/or a sequence including the amino acid sequence (L-A1). The amino acid sequence (LA2) may be an amino acid sequence including the amino acid sequences (L1-A1) of CDRL1, (L2-A1) of CDRL2, and (L3-A1) of CDRL3 and having 80% or more identity with respect to the amino acid sequence of SEQ ID NO: 20, for example. The amino acid sequence (LA2) may be an amino acid sequence including the amino acid sequence (L-A1) and having 80% or more identity with respect to the amino acid sequence of SEQ ID NO: 20, for example. The amino acid sequence (LA3) may be an amino acid sequence including the amino acid sequences (L1-A1) of CDRL1, (L2-A1) of CDRL2, and (L3-A1) of CDRL3 and in which one or several amino acids are deleted, substituted, inserted, and/or added in the amino acid sequence of SEQ ID NO: 20, for example. The amino acid sequence (LA3) may be an amino acid sequence including the amino acid sequence (L-A1) and in which one or several amino acids are deleted, substituted, inserted and/or added in the amino acid sequence of SEQ ID NO: 20, for example.

In the antibody of the present invention, for example, the heavy chain is the (HA1) and the light chain is the (LA1). The antibody of this combination is hereinafter also referred to as "3D11".

In the polypeptide of the heavy chain and the polypeptide of the light chain, the "identity" is, for example, 80% or more, 85% or more, 90% or more, 95% or more, 96% or more, 97% or more, 98% or more, or 99% or more, respectively.

In the polypeptide of the heavy chain and the polypeptide of the light chain, "one or several" relating to substitution or the like is, for example, 1 to 80, 1 to 60, 1 to 40, 1 to 30, 1 to 20, 1 to 15, 1 to 10, 1 to 9, 1 to 8, 1 to 7, 1 to 6, 1 to 5, 1 to 4, 1 to 3, 1 or 2, or 1, respectively.

Combination of (2) and (4)

The antibody or the like of the combination of (2) and (4) is also referred to as, for example, an antibody 13H11 group. In the combination of (2) and (4), the heavy chain variable region (2) includes CDRH1, CDRH2, and CDRH3, wherein CDRH1 is a polypeptide including the following amino acid sequence (H1-B), CDRH2 is a polypeptide including the following amino acid sequence (H2-B), and CDRH3 is a polypeptide including the amino following acid sequence (H3-B). Further, as described above, the light chain variable region (4) includes CDRL1, CDRL2, and CDRL3, wherein CDRL1 is a polypeptide including the amino acid sequence (L1-A), CDRL2 is a polypeptide including the amino acid sequence (L2-A), and CDRL3 is a polypeptide including the amino acid sequence (L3-A).

(H1-B) the following amino acid sequence (H1-B1), (H1-B2), or (H1-B3):

(H1-B1) an amino acid sequence of SEQ ID NO: 4 (GYAFSTSW), (H1-B2) an amino acid sequence having 80% or more identity with respect to the amino acid sequence of SEQ ID NO: 4, and (H1-B3) an amino acid sequence in which one or several amino acids are deleted, substituted, inserted and/or added in the amino acid sequence of SEQ ID NO: 4.

(H2-B) the following amino acid sequence (H2-B1), (H2-B2), or (H2-B3):

(H2-B1) an amino acid sequence of SEQ ID NO: 5 (IYPGDGDT), (H2-B2) an amino acid sequence having 80% or more identity with respect to the amino acid sequence of SEQ ID NO: 5, and (H2-B3) an amino acid sequence in which one or several amino acids are deleted, substituted, inserted and/or added in the amino acid sequence of SEQ ID NO: 5.

(H3-B) the following amino acid sequence (H3-B1), (H3-B2), or (H3-B3):

(H3-B1) an amino acid sequence of SEQ ID NO: 6 (SNDGYYVGY), (H3-B2) an amino acid sequence having 80% or more identity with respect to the amino acid sequence of SEQ ID NO: 6, and (H3-B3) an amino acid sequence in which one or several amino acids are deleted, substituted, inserted and/or added in the amino acid sequence of SEQ ID NO: 6.

In each CDR, the "identity" is, for example, 80% or more, 85% or more, 90% or more, 95% or more, 96% or more, 97% or more, 98% or more, or 99% or more.

In each CDR, "one or several" relating to substitution or the like is, for example, 1 to 5, 1 to 4, 1 to 3, 1 or 2, or 1.

In the combination of (2) and (4), the heavy chain variable region (2) includes a polypeptide consisting of the following amino acid sequence (H-B), for example. Further, the light chain variable region (4) includes a polypeptide consisting of the amino acid sequence (L-A), for example.

(H-B) the following amino acid sequence (H-B1), (H-B2), or (H-B3):

(H-B1) an amino acid sequence of SEQ ID NO: 14,

```
SEQ ID NO: 14:
QVQLQQSGPELVKPGASVKISCKASGYAFSTSWMNWVKQRPGQGLEWIG
RIYPGDGDTNYNGKFKGKATLTADKSSSTAYMQLSSLTSVDSAVYFCAR
SNDGYYVGYWGQGTTLTVSS,
```

(H-B2) an amino acid sequence having 80% or more identity with respect to the amino acid sequence of SEQ ID NO: 14, and (H-B3) an amino acid sequence in which one or several amino acids are deleted, substituted, inserted and/or added in the amino acid sequence of SEQ ID NO: 14.

The amino acid sequence (H-B1) is a sequence including the amino acid sequences (H1-B1) of CDRH1, (H2-B1) of CDRH2, and (H3-B1) of CDRH3, for example. The amino acid sequence (H-B2) may be an amino acid sequence including the amino acid sequences (H1-B1) of CDRH1, (H2-B1) of CDRH2, and (H3-B1) of CDRH3 and having 80% or more identity with respect to the amino acid sequence of SEQ ID NO: 14, for example. The amino acid sequence (H-B3) may be an amino acid sequence including the amino acid sequences (H1-B1) of CDRH1, (H2-B1) of CDRH2, and (H3-B1) of CDRH3 and in which one or several amino acids are deleted, substituted, inserted, and/or added in the amino acid sequence of SEQ ID NO: 14, for example.

In the antibody of the present invention, for example, the heavy chain variable region is the (H-B1) and the light chain variable region is the (L-A1). The antibody of this combination is hereinafter also referred to as an "antibody 13H11".

In the polypeptide of the heavy chain variable region and the polypeptide of the light chain variable region, the "identity" is, for example, 80% or more, 85% or more, 90% or more, 95% or more, 96% or more, 97% or more, 98% or more, or 99% or more, respectively.

In the polypeptide of the heavy chain variable region and the polypeptide of the light chain variable region, "one or several" relating to substitution or the like is, for example, 1 to 20, 1 to 15, 1 to 10, 1 to 9, 1 to 8, 1 to 7, 1 to 6, 1 to 5, 1 to 4, 1 to 3, 1 or 2, or 1, respectively.

In the combination of (2) and (4), the heavy chain (2) includes, for example, a polypeptide consisting of the following amino acid sequence (HB). Further, the light chain (4) includes, for example, a polypeptide consisting of the amino acid sequence (LA).

(2) a heavy chain including a polypeptide consisting of the following amino acid sequence (HB):

(HB) the following amino acid sequence (HB1), (HB2), or (HB3):

(HB1) an amino acid sequence of SEQ ID NO: 18, (HB2) an amino acid sequence having 80% or more identity with respect to the amino acid sequence of SEQ ID NO: 18, and (HB3) an amino acid sequence in which one or several amino acids are deleted, substituted, inserted and/or added in the amino acid sequence of SEQ ID NO: 18.

The amino acid sequence (HB1) is a sequence including the amino acid sequences (H1-B1) of CDRH1, (H2-B1) of CDRH2, and (H3-B1) of CDRH3 and/or a sequence including the amino acid sequence (H-B1). The amino acid sequence (HB2) may be an amino acid sequence including the amino acid sequence (H1-B1) of CDRH1, (H2-B1) of CDRH2, and (H3-B1) of CDRH3 and having 80% or more identity with respect to the amino acid sequence of SEQ ID NO: 18, for example. The amino acid sequence (HB2) may be an amino acid sequence including the amino acid sequence (H-B1) and having 80% or more identity with respect to the amino acid sequence of SEQ ID NO: 18, for example. The amino acid sequence (HB3) may be an amino acid sequence including the amino acid sequence (H1-B1) of CDRH1, (H2-B1) of CDRH2, and (H3-B1) of CDRH3 and in which one or several amino acids are deleted, substituted, inserted, and/or added in the amino acid sequence of SEQ ID NO: 18, for example. The amino acid sequence (HB3) may be an amino acid sequence including the amino acid sequence (H-B1) and in which one or several amino acids are deleted, substituted, inserted and/or added in the amino acid sequence of SEQ ID NO: 18, for example.

In the antibody of the present invention, for example, the heavy chain is the (HB1) and the light chain is the (LA1). The antibody of this combination is hereinafter also referred to as "13H11".

In the polypeptide of the heavy chain and the polypeptide of the light chain, the "identity" is, for example, 80% or more, 85% or more, 90% or more, 95% or more, 96% or more, 97% or more, 98% or more, or 99% or more, respectively.

In the polypeptide of the heavy chain and the polypeptide of the light chain, "one or several" relating to substitution or the like is, for example, 1 to 80, 1 to 60, 1 to 40, 1 to 30, 1 to 20, 1 to 15, 1 to 10, 1 to 9, 1 to 8, 1 to 7, 1 to 6, 1 to 5, 1 to 4, 1 to 3, 1 or 2, or 1, respectively.

Combination of (3) and (4)

The antibody or the like of the combination of (3) and (4) is also referred to as, for example, an antibody 15B2 group. In the combination of (3) and (4), the heavy chain variable region (3) includes CDRH1, CDRH2, and CDRH3, wherein CDRH1 is a polypeptide including the following amino acid sequence (H1-C), CDRH2 is a polypeptide including the following amino acid sequence (H2-C), and CDRH3 is a polypeptide including the following amino acid sequence (H3-C). Further, as described above, the light chain variable region (4) includes CDRL1, CDRL2, and CDRL3, wherein CDRL1 is a polypeptide including the amino acid sequence (L1-A), CDRL2 is a polypeptide including the amino acid sequence (L2-A), and CDRL3 is a polypeptide including the amino acid sequence (L3-A).

(H1-C) the following amino acid sequence (H1-C1), (H1-C2), or (H1-C3):

(H1-C1) an amino acid sequence of SEQ ID NO: 7 (GYTFTSYY), (H1-C2) an amino acid sequence having 80% or more identity with respect to the amino acid sequence of SEQ ID NO: 7, and (H1-C3) an amino acid sequence in which one or several amino acids are deleted, substituted, inserted and/or added in the amino acid sequence of SEQ ID NO: 7.

(H2-C) the following amino acid sequence (H2-C1), (H2-C2), or (H2-C3):

(H2-C1) an amino acid sequence of SEQ ID NO: 8 (INPSNGGT), (H2-C2) an amino acid sequence having 80% or more identity with respect to the amino acid sequence of SEQ ID NO: 8, and (H2-C3) an amino acid sequence in which one or several amino acids are deleted, substituted, inserted and/or added in the amino acid sequence of SEQ ID NO: 8.

(H3-C) the following amino acid sequence (H3-C1), (H3-C2), or (H3-C3):

(H3-C1) an amino acid sequence of SEQ ID NO: 9 (GYYGNPFFAY), (H3-C2) an amino acid sequence having 80% or more identity with respect to the amino acid sequence of SEQ ID NO: 9, and (H3-C3) an amino acid sequence in which one or several amino acids are deleted, substituted, inserted and/or added in the amino acid sequence of SEQ ID NO: 9.

In each CDR, the "identity" is, for example, 80% or more, 85% or more, 90% or more, 95% or more, 96% or more, 97% or more, 98% or more, or 99% or more.

In each CDR, "one or several" relating to substitution or the like is, for example, 1 to 5, 1 to 4, 1 to 3, 1 or 2, or 1.

In the combination of (3) and (4), the heavy chain variable region (3) includes a polypeptide consisting of the following amino acid sequence (H-C), for example. Further, the light chain variable region (4) includes a polypeptide consisting of the amino acid sequence (L-A), for example.

(H-C) the following amino acid sequence (H-C1), (H-C2), or (H-C3):

(H-C1) an amino acid sequence of SEQ ID NO: 15,

```
SEQ ID NO: 15:
QVQLQQSGAELVKPGASVKLSCKASGYTFTSYYMYWVKQRPGQGLEWIG
EINPSNGGTNFNEKFKNKATLTVDKSSNTAYMQLNSLTSEDSAVYYCTR
GYYGNPFFAYWGQGTLVTVSA,
```

(H-C2) an amino acid sequence having 80% or more identity with respect to the amino acid sequence of SEQ ID NO: 15, and (H-C3) an amino acid sequence in which one or several amino acids are deleted, substituted, inserted and/or added in the amino acid sequence of SEQ ID NO: 15.

The amino acid sequence (H-C1) is a sequence including the amino acid sequences (H1-C1) of CDRH1, (H2-C1) of CDRH2, and (H3-C1) of CDRH3, for example. The amino acid sequence (H-C2) may be an amino acid sequence including the amino acid sequences (H1-C1) of CDRH1, (H2-C1) of CDRH2, and (H3-C1) of CDRH3 and having 80% or more identity with respect to the amino acid sequence of SEQ ID NO: 15, for example. The amino acid sequence (H-C3) may be an amino acid sequence including the amino acid sequences (H1-C1) of CDRH1, (H2-C1) of CDRH2, and (H3-C1) of CDRH3 and in which one or several amino acids are deleted, substituted, inserted, and/or added in the amino acid sequence of SEQ ID NO: 15, for example.

In the antibody of the present invention, for example, the heavy chain variable region is the (H-C1) and the light chain variable region is the (L-A1). The antibody of this combination is hereinafter also referred to as an "antibody 15B2".

In the polypeptide of the heavy chain variable region and the polypeptide of the light chain variable region, the identity is, for example, 80% or more, 85% or more, 90% or more, 95% or more, 96% or more, 97% or more, 98% or more, or 99% or more, respectively.

In the polypeptide of the heavy chain variable region and the polypeptide of the light chain variable region, "one or several" relating to substitution or the like is, for example, 1 to 20, 1 to 15, 1 to 10, 1 to 9, 1 to 8, 1 to 7, 1 to 6, 1 to 5, 1 to 4, 1 to 3, 1 or 2, or 1, respectively.

In the combination of (3) and (4), the heavy chain (3) includes a polypeptide consisting of the following amino acid sequence (HC), for example. Further, the light chain (4) includes a polypeptide consisting of the amino acid sequence (LA), for example.

(3) a heavy chain including a polypeptide consisting of the following amino acid sequence (HC):

(HC) the following amino acid sequence (HC1), (HC2), or (HC3):

(HC1) an amino acid sequence of SEQ ID NO: 19, (HC2) an amino acid sequence having 80% or more identity with respect to the amino acid sequence of SEQ ID NO: 19, and (HC3) an amino acid sequence in which one or several amino acids are deleted, substituted, inserted and/or added in the amino acid sequence of SEQ ID NO: 19.

The amino acid sequence (HC1) is a sequence including the amino acid sequences (H1-C1) of CDRH1, (H2-C1) of CDRH2, and (H3-C1) of CDRH3, and/or a sequence including the amino acid sequence (H-C1). The amino acid sequence (HC2) may be an amino acid sequence including the amino acid sequences (H1-C1) of CDRH1, (H2-C1) of CDRH2, and (H3-C1) of CDRH3 and having 80% or more identity with respect to the amino acid sequence of SEQ ID NO: 19, for example. The amino acid sequence (HC2) may be an amino acid sequence including the amino acid sequence (H-C1) and having 80% or more identity with respect to the amino acid sequence of SEQ ID NO: 19, for example. The amino acid sequence (HC3) may be an amino acid sequence including the amino acid sequences (H1-C1) of CDRH1, (H2-C1) of CDRH2, and (H3-C1) of CDRH3 and in which one or several amino acids are deleted, substituted, inserted, and/or added in the amino acid sequence of SEQ ID NO: 19, for example. The amino acid sequence (HC3) may be an amino acid sequence including the amino acid sequence (H-C1) and in which one or several amino acids are deleted, substituted, inserted and/or added in the amino acid sequence of SEQ ID NO: 19, for example.

In the antibody of the present invention, for example, the heavy chain is the (HC1) and the light chain is the (LA1). The antibody of this combination is hereinafter also referred to as "15B2".

In the polypeptide of the heavy chain and the polypeptide of the light chain, the "identity" is, for example, 80% or more, 85% or more, 90% or more, 95% or more, 96% or more, 97% or more, 98% or more, or 99% or more, respectively.

In the polypeptide of the heavy chain and the polypeptide of the light chain, "one or several" relating to substitution or the like is, for example, 1 to 80, 1 to 60, 1 to 40, 1 to 30, 1 to 20, 1 to 15, 1 to 10, 1 to 9, 1 to 8, 1 to 7, 1 to 6, 1 to 5, 1 to 4, 1 to 3, 1 or 2, or 1, respectively.

In the present invention, the amino acid sequences of SEQ ID NOs: 1 to 20 are, for example, amino acid sequences derived from mice.

The binding between the antibody or the like of the present invention and CHIKV can be verified, for example, by a method for detecting binding between CHIKV and the antibody or the like in the description of the detection method of the present invention described below. The detection method is preferably an immunostaining method, and more preferably an indirect method. In the indirect method, for example, when the target antibody binds to CHIKV and/or when the target antibody binds to an Env protein and the signal that shows the binding thereto is strong as compared to a negative control containing no CHIKV or Env protein, the target antibody can be determined to be bound to CHIKV or an Env protein.

The antibody or the like of the present invention may further include a labeling substance, for example. The labeling substance is not particularly limited, and examples thereof include a fluorescent substance, a dye, an isotope, and an enzyme. Examples of the fluorescent substance include fluorophores such as pyrene, TAMRA, fluorescein, Cy3 dye, Cy5 dye, FAM dye, rhodamine dye, Texas red dye, JOE, MAX, HEX, TYE, and the like. Examples of the dye include Alexa dyes such as Alexa488, Alexa647 and the like.

The antibody or the like of the present invention may be immobilized on, for example, a carrier, a porous body, or the like. The carrier is not particularly limited, and examples thereof include a substrate, a bead, and a container, and examples of the container include a microplate, and a tube.

The method for producing an antibody or the like of the present invention is not particularly limited, and the antibody or the like can be produced in a genetic engineering manner based on the above-described amino acid sequence information, for example. Specifically, for example, the antibody or the like can be produced as follows. Note that the present invention is not limited to this illustration.

First, a vector containing a nucleic acid sequence encoding the amino acid sequence of each of the regions, the heavy chain, and/or the light chain in the antibody or the like of the present invention is transfected into a host to obtain a transformant. Then, the transformant is cultured, and a fraction containing an antibody that binds to the Chikungunya virus, specifically, an Env protein, is recovered, and the antibody is isolated or purified from the obtained recovered fraction.

Examples of the vector include a vector containing a nucleic acid sequence encoding the heavy chain variable region, a vector containing a nucleic acid sequence encoding the light chain variable region, a vector containing a nucleic acid sequence encoding the heavy chain, and a vector containing a nucleic acid sequence encoding the light chain. The host is not particularly limited and may be any host into which the vector can be transfected and in which the nucleic acid sequence in the vector can be expressed. Examples of the host include mammalian cells such as HEK cells, CHO cells, COS cells, NSO cells, SP2/0 cells, and the like. The method for transfecting the vector into a host is not particularly limited, and known methods can be employed.

The method for culturing the transformant is not particularly limited, and can be appropriately determined depending on the type of the host. A fraction containing the antibody can be recovered as a liquid fraction by crushing the cultured transformant, for example. Isolation or purification of the antibody is not particularly limited, and known methods can be employed.

In the present invention, the antibody is, for example, a monoclonal antibody. Examples of the monoclonal antibody include a monoclonal antibody obtained by immunizing an animal, a chimeric antibody, a humanized antibody, and a human antibody (also referred to as a fully human antibody).

The chimeric antibody is an antibody obtained by linking a variable region of an antibody derived from a non-human animal and a constant region of a human antibody. The chimeric antibody can be produced, for example, as follows. First, a gene of a variable region (V region) of a monoclonal antibody derived from a non-human animal that binds to Chikungunya virus, specifically, an Env protein, is prepared, the gene of the variable region is linked to a gene of a constant region (C region) of a human antibody, and the resultant is further linked to an expression vector. Then, the cells transfected with the expression vector are cultured, and the target chimeric antibody secreted into the culture solution is recovered, thereby preparing the chimeric antibody. The animal from which the gene of the variable region is derived is not particularly limited, and examples thereof include rats and mice. The method for producing the chimeric antibody is not limited thereto, and can be produced with reference to a known method such as a method described in JPH3(1991)-73280A, for example.

The humanized antibody is an antibody in which only the CDR is derived from a non-human animal and the other region is derived from a human. The humanized antibody can be produced, for example, as follows. First, a gene of the CDR of a monoclonal antibody from a non-human animal is prepared and transplanted (CDR-grafting) into a gene of a human antibody, e.g., a constant region, and the resultant is further linked to an expression vector. Then, by culturing the cells transfected with the expression vector, a humanized antibody transplanted with the target CDR is secreted into the culture solution. By recovering the secreted antibody, the humanized antibody can be prepared. The animal from which the CDR is derived is not particularly limited, and examples thereof include rats and mice. The method for producing a humanized antibody is not limited thereto, and can be produced with reference to known methods such as methods described in JPH4(1992)-506458A, JPS62(1987)-296890A, and the like, for example.

The human antibody is an antibody in which the entire region is of human origin. The human antibody can be produced by transfecting a human antibody gene into a non-human animal, for example. As the animal to be transfected with the human antibody gene, for example, a transgenic animal for human antibody production can be used. The type of the animal is not particularly limited, and the animal may be, for example, a mouse. As to the method for producing the human antibody, reference can be made to known methods such as methods described in, for example, Nature Genetics, Vol. 7, p. 13-21, 1994; Nature Genetics, Vol. 15, p. 146-156, 1997; JPH4(1992)-504365A; JPH7(1995)-509137A; WO94/25585; Nature, Vol. 368, p. 856-859, 1994; and JPH6(1994)-500233A. Also, the human antibody can be produced using a phage display method, for example. The human antibody can be produced with reference to a known method described in Marks, J. D. et al: J. Mol. Biol., Vol. 222, p. 581-59'7, 1991, for example.

The antibody or the like of the present invention can also be prepared by immunizing an animal with an antibody, for example. The antigen is, for example, Chikungunya virus, specifically, a protein consisting of the full-length amino acid sequence of the Env protein or a peptide fragment thereof. Preferably, the antigen is immunized multiple times. In this case, the antigen to be immunized each time is preferably Chikungunya virus or an Env protein of different genotypes, or a peptide fragment thereof, for example. The peptide fragment may be, for example, a peptide fragment consisting solely of an antigenic determinant (epitope) or a peptide fragment including the antigenic determinant.

The monoclonal antibody obtained by immunization on an animal can be produced with reference to a known method such as the method described in "Current Protocols in Molecular Biology" (John Wiley & Sons (1987)), Antibodies: A Laboratory Manual, Ed. Harlow and David Lane, Cold Spring Harbor Laboratory(1988)), for example. Specifically, for example, an animal is immunized with an antigen, and antibody-producing cells collected from the immunized animal are fused with myeloma cells lacking the ability to produce an autoantibody, thereby producing a hybridoma. Subsequently, antibody-producing cells are screened from the hybridoma to produce a single clone of hybridoma by cloning. Then, the hybridoma clone is administered to an animal, and a monoclonal antibody is purified from the obtained peritoneal cavity. Alternatively, the hybridoma is cultured, and a monoclonal antibody is purified from the culture solution thereof. Thus, by producing the hybridoma clone, a monoclonal antibody having uniform specificity can be stably supplied.

Preferably, the myeloma cells are derived from, for example, mice, rats, humans, and the like. The myeloma cells and the antibody-producing cells may be derived from the same or different species, for example, but are preferably derived from the same species.

The antibody or the like of the present invention may be, in place of the above-described antibody or the like of the present invention, an antibody against Chikungunya virus that binds to ECSA type CHIKV, WA type CHIKV, and Asian type CHIKV and that does not bind to Sindbis virus or an anti-binding fragment of the antibody, for example. More specifically, the antibody or the like of the present invention may be, for example, an antibody or the like that binds to an Env protein of ECSA type CHIKV, an Env protein of WA type CHIKV, and an Env protein of Asian type CHIKV and that does not bind to Sindbis virus. The antibody or the like of the present invention may be, in place of the above-described antibody or the like of the present invention, an antibody that binds to ECSA type CHIKV, WA type CHIKV, and Asian type CHIKV, that does not bind to Sindbis virus, and that competes with a reference antibody for the binding to ECSA type CHIKV, WA type CHIKV, and Asian type CHIKV, for example, wherein the reference antibody may be the above-described antibody or the like of the present invention, i.e., the antibody 3D11 group, the antibody 13H11 group, or the antibody 15B2 group, the antibody 3D11, the antibody 13H11, or the antibody 15B2, or 3D11, 13H11, or 15B2. The antibody or the like of the present invention may be, in place of the above-described antibody or the like of the present invention, an antibody that binds to an Env protein of ECSA type CHIKV, an Env protein of WA type CHIKV, and an Env protein of Asian type CHIKV, that does not bind to Sindbis virus, and that competes with a reference antibody for the binding to an Env protein of ECSA type CHIKV, an Env protein of WA type CHIKV, and an Env protein of Asian type CHIKV, for example, wherein the reference antibody may be the above-described antibody or the like of the present invention, i.e., the antibody 3D11 group, the antibody 13H11 group, or the antibody 15B2 group, the antibody 3D11, the antibody 13H11 or the antibody 15B2, or 3D11, 13H11 or 15B2. The Env protein of ECSA type CHIKV may be, for example, a protein consisting of the amino acid sequence of SEQ ID NO: 21. The Env protein of WA type CHIKV may be, for example, a protein consisting of the amino acid sequence of SEQ ID NO: 22. The Env protein of Asian type CHIKV may be, for example, a protein consisting of the amino acid sequence of SEQ ID NO: 23. The SINV may be, for example, the strain R68 to be described below.

Gene, Expression Vector, and Transformant

The coding gene of the present invention is a coding gene for an antibody against Chikungunya virus or an antigen-binding fragment of the antibody, and includes a polynucleotide encoding the amino acid sequence of the antibody or the antigen-binding fragment of the present invention.

By expressing the coding gene of the present invention, the antibody or the like of the present invention can be obtained. The sequence of the coding gene of the present invention is not particularly limited, and any sequence may be used as long as it encodes the amino acid sequence of the antibody or the like of the present invention, and may be a sense sequence or an antisense sequence.

The expression vector of the present invention is an expression vector of an antibody against Chikungunya virus or an antigen-binding fragment of the antibody, and includes the coding gene of the present invention. In the expression vector, the coding gene is linked to the linking vector in such a manner to be capable of expressing the antibody or the antigen-binding fragment of the antibody of the invention. The expression vector of the present invention may be any vector as long as it is capable of expressing the antibody or the like of the present invention, and other configurations are not particularly limited.

The expression vector of the present invention may be, for example, an expression vector including a nucleic acid sequence encoding the heavy chain variable region and a nucleic acid sequence encoding the light chain variable region, or may be a set of an expression vector including a nucleic acid sequence encoding the heavy chain variable region and an expression vector including a nucleic acid sequence encoding the light chain variable region. The expression vector of the present invention can be prepared, for example, by linking the coding gene of the invention to a linking vector. The type of the linking vector linking to the coding gene is not particularly limited, and may be, for example, pUC. The linking vector may be appropriately set, for example, depending on a host into which the expression vector is transfected. The host is not particularly limited, and examples thereof include mammalian cells such as CHO cells.

The transformant of the present invention is a transformant expressing the antibody or the like of the present invention, and includes a host and the coding gene of the present invention. The transformant of the present invention may include the coding gene of the present invention in such a manner to be capable of expressing. Preferably, the transformant includes the expression vector of the present invention, for example. The method for transfecting the expression vector into the host is not particularly limited, and known methods can be employed.

Detection Kit

The detection kit for Chikungunya virus of the present invention includes the antibody or the antigen-binding fragment of the antibody of the present invention, as described above. The detection kit of the present invention is characterized in that it includes the antibody or the like of the present invention, and other configurations and conditions are not particularly limited. According to the kit of the present invention, for example, the detection method of the present invention described below can be conveniently performed. Regarding the detection kit of the present invention, for example, reference can be made to the description as to the antibody or the like of the present invention.

The detection kit of the present invention may further include, for example, a detection substance that detects binding between CHIKV and the antibody or the like of the present invention, more specifically, binding between the Env protein and the antibody or the like of the invention, for example. The detection substance may be, for example, a combination of a detectable labeled antibody to the antibody or the like and a substrate or the like to the label.

The detection kit of the present invention may include other components in addition to the antibody or the like of the present invention, for example. Such components include, for example, the carriers, buffers, instructions for use, and the like.

In the detection kit of the present invention, for example, the antibody or the like and other components such as the buffer may be contained in separate containers or may be contained in the same container in a mixed or unmixed manner. When the antibody or the like and the other components are mixed and contained in the same container, the detection kit of the present invention can also be referred to as a detection reagent.

Detection Method

The method for detecting Chikungunya virus of the present invention, includes: a detection step of bringing a sample into contact with the antibody or the antigen-binding fragment of the antibody according to the present invention to bind Chikungunya virus in the sample to the antibody or the antigen-binding fragment of the antibody, thereby detecting Chikungunya virus in the sample. The detection method of the present invention is characterized in that the antibody or the antigen-binding fragment of the antibody of the present invention is used, and other steps and conditions are not particularly limited. Regarding the detection method of the present invention, reference can be made to the description as to the antibody, detection kit, or the like of the present invention.

The detection method of the present invention uses the antibody or the like of the present invention. The antibody or the like binds to ECSA type CHIKV, WA type CHIKV, and Asian type CHIKV, and more specifically binds to an Env protein of ECSA type CHIKV, an Env protein of WA type CHIKV, and an Env protein of Asian type CHIKV, for example. Thus, the detection method of the present invention can indirectly detect CHIKV by detecting an Env protein of CHIKV, for example. According to the detection method of the present invention, any of the ECSA type CHIKV, the WA type CHIKV, and the Asian type CHIKV can be detected. The antibody or the like does not bind to Sindbis virus, for example. Thus, the detection method of the present invention can reduce the possibility of erroneously detecting a sample containing a SINV as including a CHIKV as compared to a case of using a CK119 antibody, for example. Further, the antibody or the like of the present invention binds to an Env protein, for example. Thus, the detection method of the present invention can also be referred to as a method for detecting an Env protein.

According to the detection method of the present invention, it is possible to analyze the presence or absence of CHIKV or the amount of CHIKV in a sample. Thus, the detection method of the present invention can also be referred to as an analysis method, for example.

In the detection method of the present invention, the origin of the sample is not particularly limited, and examples thereof include humans and non-human animals, and examples of the non-human animals include mammals such as a mouse, a rat, a dog, a monkey, a rabbit, a sheep, a horse, and the like as described above.

The type of the sample is not particularly limited, and examples thereof include biological samples such as body fluids, urine, body fluid-derived cells, organs, tissues, and cells separated from a living body. Examples of the body fluid include body cavity fluid such as blood, synovial fluid, and the like, lymph, and tissue fluid, and specific examples thereof include whole blood, serum, and plasma. The biological sample is preferably whole blood, serum, or plasma, and more preferably serum or plasma. For example, as to the sample, the collected sample may be used as it is in the detection method of the present invention, or may be used after performing other treatment such as dilution with a liquid or the like. The liquid is not particularly limited, and examples thereof include water, physiological saline, a buffer, and a medium. In addition, the sample may be subjected to an acid treatment in advance, for example. Thereby, in the detection method of the present invention, for example, the antibody and the Chikungunya virus can be dissociated when the Chikungunya virus in the sample and the antibody form an antigen-antibody complex, so that the Chikungunya virus can be detected with more sensitivity. The acid used in the acid treatment is not particularly limited, and examples thereof include hydrochloric acid and acetic acid.

The sample may be, for example, a sample containing CHIKV, a sample containing no CHIKV, or a sample which is unknown whether it contains CHIKV or not.

The sample may be, for example, a liquid sample or a solid sample. In the case of the solid sample, for example, it is preferable to mix with the liquid and use it as a liquid sample because in that way the sample can easily be contact with the antibody or the like and is easy to handle.

The detection step includes, for example, a contact step of bringing the sample into contact with the antibody or the like to bind CHIKV in the sample to the antibody or the like, and a binding detection step of detecting binding between CHIKV and the antibody or the like. Also, the detection step further includes a step of analyzing the presence or absence of CHIKV or the amount of CHIKV in the sample based on the result of the binding detection step.

In the contact step, a method for bringing the sample into contact with the antibody or the like is not particularly limited. The contact between the sample and the antibody or the like is preferably performed in a liquid, for example. The liquid is not particularly limited, and examples thereof include water, physiological saline, and a buffer.

In the contact step, the contact conditions between the sample and the antibody or the like are not particularly limited. The contact temperature is, for example, 4° C. to 37° C. The contact time is, for example, 10 to 120 minutes. The concentration of the antibody or the like in the mixture of the sample and the antibody or the like is not particularly limited, and is, for example, 0.1 m/ml to 1 mg/ml.

In the contact step, the antibody or the like may be, for example, an immobilized antibody or the like which is immobilized on a carrier, or an unimmobilized free antibody or the like. In the latter case, the antibody or the like is brought into contacted with the sample in a container, for example. The antibody or the like is preferably the immobilized antibody or the like because it is excellent in handleability, for example. The carrier is not particularly limited, and examples thereof include substrates, beads, and containers, and examples of the container include microplates and tubes.

The binding detection step is a step of detecting binding between CHIKV in the sample and the antibody or the like, as described above. By detecting whether or not there is binding therebetween, for example, the presence or absence of CHIKV in the sample can be analyzed (qualitative analysis can be performed), and by detecting the degree (binding amount) of binding therebetween, for example, the amount of CHIKV in the sample can be analyzed (quantitative analysis can be performed).

Then, when the binding between CHIKV and the antibody or the like cannot be detected, it can be determined that the sample contains no CHIKV, and when the binding is detected, it can be determined that the sample contains CHIKV. In addition, it is also possible to obtain the relationship between the number of CHIKV and the binding amount in advance, and to analyze the amount of CHIKV in the sample from the binding amount based on the relationship.

The method for detecting the binding between CHIKV and the antibody or the like is not particularly limited, and for example, a known method of utilizing binding between an antibody or an antigen-binding fragment and an antigen can be employed. Specific examples of the detection method include an immunoantibody method, an immunostaining method, an ELISA method, a flow cytometry, and a Western blotting method.

When the sample is a biological sample derived from a subject, for example, the detection method of the present invention may include a test step of testing a risk of CHIKV infection of the subject by comparing the amount of CHIKV in a biological sample of the subject (hereinafter, also referred to as a subject biological sample) with a reference value. In this case, the detection method of the present invention can also be referred to as, for example, a method for testing the risk of CHIKV infection. The reference value is not particularly limited, and may be, for example, the amount of CHIKV in a healthy subject, a CHIKV infected subject, or the like. In the case of prognostic assessment, the reference value may be, for example, the amount of CHIKV after treatment of the same subject.

The reference value can be obtained, for example, using a biological sample isolated from a healthy subject and/or an infected subject (hereinafter, also referred to as a "reference biological sample") as described above. The reference value may be measured simultaneously with, for example, a subject biological sample of the subject, or may be measured in advance. The latter case is preferable because it is unnecessary to obtain a reference value every time the subject biological sample of the subject is measured, for example. It is preferable that the subject biological sample of the subject and the reference biological sample be collected under the same conditions, for example, and the detection (e.g., quantitative analysis) of CHIKV is performed under the same conditions.

In the test step, a method for assessing the risk of CHIKV infection of a subject is not particularly limited, and can be appropriately determined according to the type of the reference value. Specifically, when the amount of CHIKV in the subject biological sample of the subject is significantly higher than the amount of CHIKV in the reference biological sample of the healthy subject, when the amount of CHIKV in the subject biological sample of the subject is the same as the amount of CHIKV in the reference biological sample of the infected subject (when there is no significant difference therebetween), and/or when the amount of CHIKV in the subject biological sample of the subject is significantly higher than the amount of CHIKV in the reference biological sample of the infected subject, the subject can be assessed as at risk or at high risk of CHIKV infection. On the other hand, when the amount of CHIKV in the subject biological sample of the subject is the same as the amount of CHIKV in the reference biological sample of the healthy subject (when there is no significant difference therebetween), when the amount of CHIKV in the subject biological sample of the subject is significantly lower than the amount of CHIKV in the reference biological sample of the healthy subject, and/or when the amount of CHIKV in the subject biological sample of the subject is significantly lower than the amount of CHIKV in the reference biological sample of the infected subject, the subject can be assessed as having no risk or a low risk of CHIKV infection.

In the test step, in the case of prognostic assessment, for example, the assessment can be made in the same manner as described above or by using the amount of CHIKV in a reference biological sample after treatment of the same subject as a reference value. As a specific example, when the amount of CHIKV in the subject biological sample of the subject is significantly higher than the reference value, the subject can be assessed as at risk of relapse or deterioration (becoming severe) after the treatment. Also, when the amount of CHIKV in the subject biological sample of the subject is the same as the reference value (when there is no significant difference therebetween) and/or when the amount of CHIKV in the subject biological sample of the subject is significantly lower than the reference value, the subject can be assessed as having no risk or a low risk of relapse after the treatment.

In the present invention, for example, biological samples of the same subject may be collected over time, and the amounts of CHIKV in the biological samples may be compared. Thereby, for example, it is possible to judge that the possibility of becoming severe increases if the expression level increases over time, and it is possible to judge that the possibility of becoming severe decreases or that the subject has healed if the expression level decreases over time.

Diagnostic Method and Diagnostic Kit for Chikungunya Virus

The diagnostic method for Chikungunya virus of the present invention includes a detection step of bringing a sample into contact with the antibody or the antigen-binding fragment of the antibody of the present invention to bind Chikungunya virus in the sample to the antibody or the antigen-binding fragment of the antibody, thereby detecting Chikungunya virus in the sample. Further, the diagnostic kit for Chikungunya virus of the present invention includes the antibody or the antigen-binding fragment of the antibody of the present invention. Regarding the diagnostic method and the diagnostic kit, reference can be made to the description as to the antibody or the like, the detection kit, the detection method, and the like of the present invention.

EXAMPLES

The examples of the present invention are described below. The present invention, however, is not limited by the following examples. Commercially available reagents were used based on their protocols unless otherwise indicated.

Example 1

The anti CHIKV antibody of the present invention was produced. General methods were employed unless otherwise indicated.

As antigens, cultured cells infected with ECSA type CHIKV and Sendai virus expressing 6K-E1 protein of Asian type CHIKV were used. Specifically, mice (Balb/c) aged 4 to 6 weeks were immunized with a mixture of the cultured cells and CFA (Complete Freund's adjuvant) for the first time. Two weeks after the first immunization, the mice were immunized with a mixture of the cultured cells and IFA (Incomplete Freund's adjuvant) for the second time. Two weeks after the second immunization, the mice were immunized with a mixture of the virus and IFA for the third time. Three days after the third immunization, B cells were prepared from the mice and hybridomas were prepared from the B cells by a conventional method. The resulting hybridomas were screened for anti CHIKV antibody-producing hybridomas using their culture solution.

Consequently, three hybridomas (3D11, 13H11, and 15B2 strains) were isolated. Three monoclonal antibodies (3D11, 13H11, and 15B2) were obtained as anti CHIKV antibodies generated from these hybridomas. The isotypes of 3D11, 13H11, and 15B2 were IgG2aκ, IgG1κ, and IgG2bκ, respectively.

Amino acid sequences were determined for the anti CHIKV antibodies 3D11, 13H11, and 15B2. The results thereof are shown below. The light chains 3D11, 13H11, and 15B2 all have the same amino acid sequence. In each amino acid sequence, the underlined amino acid sequences correspond to the amino acid sequences of CDR1, CDR2 and CDR3, respectively, from the N-terminus toward the C-terminus. In addition, in each amino acid sequence, an amino acid sequence enclosed in parentheses corresponds to an amino acid sequence of a variable region.

3D11 heavy chain (SEQ ID NO: 17)

[QVQLQQSGAELARPGASVKLSCKASGYTFTSYWMQWVKQRPGQGLEWI
GAIYPGDGDTRYTQKFKGKATLTADKSSSTAYMQLSSLASEDSAVYYCA
RSYDPFDYWGQGTTLTVSS]AKTTAPSVYPLAPVCGDTTGSSVTLGCLV
KGYFPEPVTLTWNSGSLSSGVHTFPAVLQSDLYTLSSSVTVTSSTWPSQ
SITCNVAHPASSTKVDKKIEPRGPTIKPCPPCKCPAPNLLGGPSVFIFP
PKIKDVLMISLSPIVTCVVVDVSEDDPDVQISWFVNNVEVHTAQTQTHR
EDYNSTLRVVSALPIQHQDWMSGKEFKCKVNNKDLPAPIERTISKPKGS
VRAPQVYVLPPPEEEMTKKQVTLTCMVTDFMPEDIYVEWTNNGKTELNY
KNTEPVLDSDGSYFMYSKLRVEKKNWVERNSYSCSVVHEGLHNHEITTK
SFSRTPGK

13H11 heavy chain (SEQ ID NO: 18)

[QVQLQQSGPELVKPGASVKISCKASGYAFSTSWMNWVKQRPGQGLEWI
GRIYPGDGDTNYNGKFKGKATLTADKSSSTAYMQLSSLTSVDSAVYFCA
RSNDGYYVGYWGQGTTLTVSS]AKTTPPSVYPLAPGSAAQTNSMVTLGC
LVKGYFPEPVTVTWNSGSLSSGVHTFPAVLQSDLYTLSSSVTVPSSTWP
SETVTCNVAHPASSTKVDKKIVPRDCGCKPCICTVPEVSSVFIFPPKPK
DVLTITLTPKVTCVVVDISKDDPEVQFSWFVDDVEVHTAQTQPREEQFN
STFRSVSELPIMHQDWLNGKEFKCRVNSAAFPAPIEKTISKTKGRPKAP
QVYTIPPPKEQMAKDKVSLTCMITDFFPEDITVEWQWNGQPAENYKNTQ
PIMDTDGSYFVYSKLNVQKSNWEAGNTFTCSVLHEGLHNHHTEKSLSHS
PGK

15B2 heavy chain (SEQ ID NO: 19)

[QVQLQQSGAELVKPGASVKLSCKASGYTFTSYYMYWVKQRPGQGLEWI
GEINPSNGGTNFNEKFKNKATLTVDKSSNTAYMQLNSLTSEDSAVYYCT
RGYYGNPFFAYWGQGTLVTVSA]AKTTPPSVYPLAPGCGDTTGSSVTLG
CLVKGYFPESVTVTWNSGSLSSSVHTFPALLQSGLYTMSSSVTVPSSTW
PSQTVTCSVAHPASSTTVDKKLEPSGPISTINPCPPCKECHKCPAPNLE
GGPSVFIFPPNIKDVLMISLTPKVTCVVVDVSEDDPDVQISWFVNNVEV
HTAQTQTHREDYNSTIRVVSTLPIQHQDWMSGKEFKCKVNNKDLPSPIE
RTISKIKGLVRAPQVYILPPPAEQLSRKDVSLTCLVVGFNPGDISVEWT
SNGHTEENYKDTAPVLDSDGSYFIYSKLNMKTSKWEKTDSFSCNVRHEG
LKNYYLKKTISRSPGK

-continued

3D11, 13H11, and 15B2 light chain (SEQ ID NO: 20)

[NIVMTQSPKSMSMSVGERVTLTCKASENVVTYVSWYQQKPEQSPKLLI
YGASNRYTGVPDRFTGSGSATDFTLTISSVQAEDLADYHCGQGYSYPYT
FGGGTKLEI]KRADAAPTVSIFPPSSEQLTSGGASVVCFLNNFYPKDIN
VKWKIDGSERQNGVLNSWTDQDSKDSTYSMSSTLTLTKDEYERHNSYTC
EATHKTSTSPIVKSFNRNEC

In the following examples, the hybridoma was administered to a mouse peritoneal cavity, and an antibody purified from the obtained ascites fluid was used as an antibody sample.

Example 2

It was examined that the antibody of the present invention binds to an Env protein of CHIKV of each genotype by indirect immunofluorescence assays (immunostaining method).

(1) Vector Preparation

Expression vectors containing an Env protein of CHIKV or a capsid protein of CHIKV were prepared in the following manner. Specifically, a codon-optimized cDNA was prepared for each cDNA encoding a capsid protein of CHIKV, or an Env protein of ECSA type (CP10 strain), WA type (37997 strain), or Asian type (CK12-686 strain). Regarding cDNA encoding the Env protein, reference was made to the nucleic acid sequence information registered in NCBI. Specifically, regarding the Env protein of ECSA type (CP10 strain), reference was made to the nucleic acid sequence information registered in NCBI Accession NO.: AB857761.1. Regarding the Env protein of WA type (37997 strain), reference was made to the genomic information registered with NCBI Accession NO.: AY726732. Regarding the Env protein of Asian type (CK12-686 strain), reference was made to the genomic information registered in NCBI Accession No.: CWIH01000001.1. A cDNA cassette encoding a capsid protein of CHIKV or an Env protein of CHIKV were transfected into pCAGGS MSII plasmid. An expression vector containing a mutant Env protein (E350D) or a mutant Env protein (D350E) was produced using an overlap primer. In the Env protein of CP10 strain, glutamic acid (E) was substituted with aspartic acid (D). In the Env proteins of CK12-686 strain and 37997 strain, aspartic acid (D) was substituted with glutamic acid (E).

(2) Preparation of Env Protein Expressing Cells

HEK293T cells were seeded in 96 well plates so as to achieve a density of $2\times10^4$ cells/100 μl/well. The culture solution was a DMEM medium (manufactured by Dulbecco's Modified Eagle Medium, Life technologies) containing 10% (v/v) heat-inactivated fetal bovine serum (FBS, manufactured by Life Technologies). Culture conditions were 37° C. and 5% $CO_2$ (hereinafter, the same applies). At 20 hours of the seeding, the expression vector and transfection reagent (Lipofectamine® 2000, manufactured by Invitrogen Co., Ltd.) were used and transfected into HEK293T cells according to the attached protocol.

(3) Indirect Immunofluorescence Assays

Forty-eight hours after the transfection, cells in each well were immobilized using a phosphate buffer (PBS) with 3.7%

(v/v) formaldehyde and then subjected to permeabilization using 1% Triton® X-100. Purified 3D11, 13H11, or 15B2 was added as a primary antibody to obtain 50 μl of supernatant or 2 μg/ml solution and the resultant was incubated for 1 hour at 37° C.

After the incubation, each well was washed with PBS and 50 μl of secondary antibody was added. The secondary antibody was an Alexa Flour 488-labeled goat anti-mouse IgG antibody (manufactured by Invitrogen). After the addition, the resultant was incubated at 37° C. for 45 minutes. Next, each well was washed with PBS, and each well was observed using a fluorescent microscope (IX71, manufactured by Olympus Co., Ltd.). The results of cells expressing the Env protein are shown in FIGS. 1A to 1C.

FIGS. 1A to 1C show photographs showing the staining results of cells expressing Env protein. FIG. 1A shows the staining results of 3D11, FIG. 1B shows the staining results of 13H11, and FIG. 1C shows the staining results of 15B2. In FIGS. 1A to 1C, the photographs show the results of cells expressing (1) Env protein of ECSA type, (2) mutant Env protein of ECSA type E350D, (3) Env protein of WA type, (4) mutant Env protein of WA type D350E, (5) Env protein of Asian type, and (6) mutant Env protein of Asian type D350E from the left column to the right column. Arrows in FIGS. 1A to 1C indicate examples of cells each stained with each antibody. In FIGS. A to 1C, as indicated by the arrows, 3D11, 13H11, and 15B2 were found to bind to any of the Env proteins. These results show that the antibody or the like of the present invention can be used for detecting three genotypes of CHIKV, more specifically, Env proteins of three genotypes of CHIKV. Although it is not shown, none of the antibodies stained the vector non-transfected cells and cells expressing the capsid protein.

In addition, as to cells expressing Env protein, when the results of staining with CK47 antibody or CK119 antibody and the results of staining with 3D11, 13H11, and 15B2 were compared, 3D11, 13H11, and 15B2 stained strongly the intracytoplasmic regions in addition to the cell surface as in the case of CK47 antibody or CK119 antibody, although it is not shown. This was presumed by the fact that, unlike CK47 antibody or CK119 antibody, 3D11, 13H11, and 15B2 also bind to the Env protein misfolding protein. This presumption does not limit the present invention in any way.

Example 3

It was examined whether the antibody of the present invention does not bind to SINV by indirect immunofluorescence assays (immunostaining method).

(1) Preparation of SINV-Infected Cells

Baby Hamster Kidney fibroblast cell line (BHK) cells were seeded in 96 well plates so as to achieve a density of $2\times10^4$ cells/100 μl/well. SINV (R68 strain, obtained from Professor Kohji Morishi of Yamanashi University) was immunized with BHK cells at MOI 0.01 to prepare SINV-infected cells. BHK cells were cultured in a DMEM medium containing 10% (v/v) heat-inactivated FBS when it was not infected with SINV. BHK cells were cultured in a DMEM medium containing 2% (v/v) heat-inactivated FBS after being infected with SINV.

(2) Indirect Immunofluorescence Assays

SINV-infected cells were stained in the same manner as in Example 2(3) except that SINV-infected cells were used instead of cells after transfection, and each well was observed using the fluorescent microscope. The results are shown in FIGS. 2A to 2D.

Figure 2A:
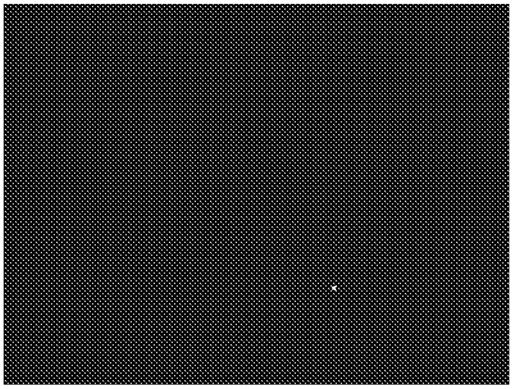
FIGS. 2A to 2D show photographs showing the staining results of SINV-infected cells in Example 3.
Figure 2B:
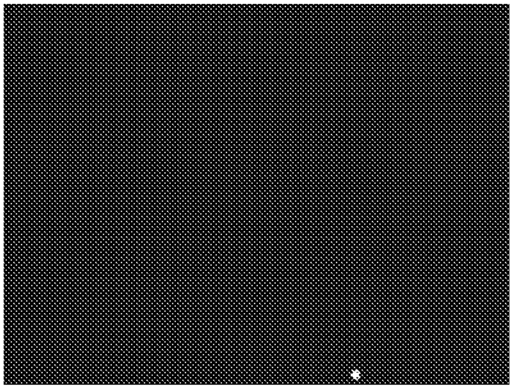
Figure 2C:
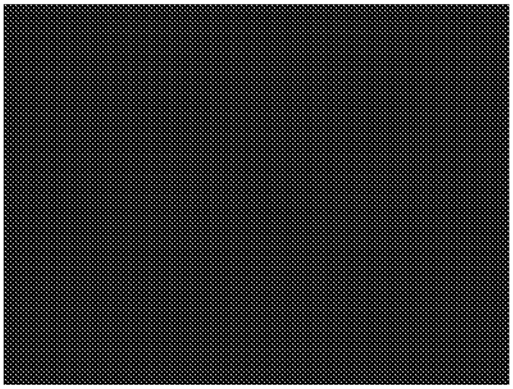
Figure 2D:
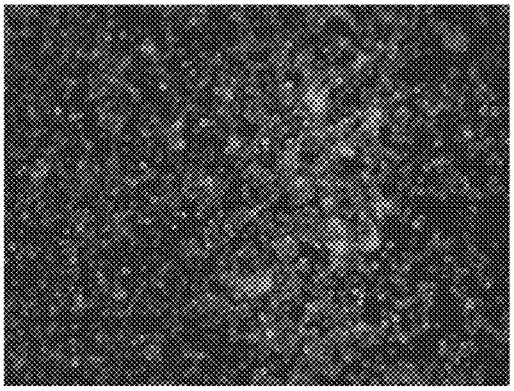

FIGS. 2A to 2D show photographs showing the staining results of SINV-infected cells. FIG. 2A shows the staining result of 3D11, FIG. 2B shows the staining result of 13H11, FIG. 2C shows the staining result of 15B2, and FIG. 2D shows the staining result of CK119 antibody. As shown in FIG. 2D, CK119 antibody stained SINV-infected cells and showed cross-reactivity with SINV. In contrast, as shown in FIGS. 2A to 2C, 3D11, 13H11, and 15B2 did not stain SINV-infected cells and showed no cross-reactivity with SINV. These results show that the antibody or the like of the present invention does not bind to SINV.

While the present invention has been described above with reference to illustrative embodiments, the present invention is by no means limited thereto. Various changes and variations that may become apparent to those skilled in the art may be made in the configuration and specifics of the present invention without departing from the scope of the present invention.

This application claims priority from Japanese Patent Application No. 2018-022084 filed on Feb. 9, 2018. The entire subject matter of the Japanese Patent Application is incorporated herein by reference.

INDUSTRIAL APPLICABILITY

As described above, the antibody or the like of the present invention binds to three genotypes of CHIKV, namely ECSA type CHIKV, WA type CHIKV, and Asian type CHIKV. Thus, according to the antibody or the like of the present invention, for example, CHIKV can be detected regardless of the genotype, and therefore, it can be suitably used for a detection kit for CHIKV. Therefore, the present invention is extremely useful in the field of clinical testing and the like.

SEQUENCE LISTING

..¥Sequence List/Drawings¥TF18002WO_Sequence Listing_ST25.txt

The invention claimed is:

1. An antibody against Chikungunya virus or an antigen-binding fragment of the antibody, comprising the following heavy chain variable region (1), (2), or (3) and the following light chain variable region (4):

(1) a heavy chain variable region comprising heavy chain complementarity determining regions (CDRHA)-1, CDRHA-2, and CDRHA-3:

CDRHA-1 is a polypeptide comprising the following amino acid sequence (H1-A1),

CDRHA-2 is a polypeptide comprising the following amino acid sequence (H2-A1), and CDRHA-3 is a polypeptide comprising the following amino acid sequence (H3-A1):

(H1-A1) an amino acid sequence of SEQ ID NO: 1 (GYTFTSYW), (H2-A1) an amino acid sequence of SEQ ID NO: 2 (IYPGDGDTRYT), and (H3-A1) an amino acid sequence of SEQ ID NO: 3 (SYDPFDY), (2) a heavy chain variable region comprising CDRHB-1, CDRHB-2, and CDRHB-3:

CDRHB-1 is a polypeptide comprising the following amino acid sequence (H1-B1),

CDRHB-2 is a polypeptide comprising the following amino acid sequence (H2-B1), and CDRHB-3 is a polypeptide comprising the following amino acid sequence (H3-B1):

(H1-B1) an amino acid sequence of SEQ ID NO: 4 (GYAFSTSW), (H2-B1) an amino acid sequence of SEQ ID NO: 5 (IYPGDGDT), and (H3-B1) an amino acid sequence of SEQ ID NO: 6 (SNDGYYVGY), (3) a heavy chain variable region comprising CDRHC-1, CDRHC-2, and CDRHC-3:

CDRHC-1 is a polypeptide comprising the following amino acid sequence (H1-C1),

CDRHC-2 is a polypeptide comprising the following amino acid sequence (H2-C1), and CDRHC-3 is a polypeptide comprising the following amino acid sequence (H3-C1):

(H1-C1) an amino acid sequence of SEQ ID NO: 7 (GYTFTSYY), (H2-C1) an amino acid sequence of SEQ ID NO: 8 (INPSNGGT), and (H3-C1) an amino acid sequence of SEQ ID NO: 9 (GYYGNPFFAY), (4) a light chain variable region comprising light chain complementarity determining regions (CDRL)-1, CDRL-2, and CDRL-3:

CDRL-1 is a polypeptide comprising the following amino acid sequence (L1-A1),

CDRL-2 is a polypeptide comprising the following amino acid sequence (L2-A1), and CDRL-3 is a polypeptide comprising the following amino acid sequence (L3-A1):

(L1-A1) an amino acid sequence of SEQ ID NO: 10 (ENVVTY), (L2-A1) an amino acid sequence of SEQ ID NO: 11 (GAS), and (L3-A1) an amino acid sequence of SEQ ID NO: 12 (GQGYSYPYT).

2. An antibody against Chikungunya virus or an antigen-binding fragment of the antibody, comprising the following heavy chain variable region (1), (2), or (3) and the following light chain variable region (4):

(1) a heavy chain variable region comprising a polypeptide consisting of the following amino acid sequence (H-A) that is selected from the group consisting of amino acid sequences (H-A1), (H-A2), and (H-A3):

(H-A1) an amino acid sequence of SEQ ID NO: 13, (H-A2) an amino acid sequence having 80% or more identity with respect to the amino acid sequence of SEQ ID NO: 13, and (H-A3) an amino acid sequence in which one to twenty amino acids are deleted, substituted, inserted and/or added in the amino acid sequence of SEQ ID NO: 13, wherein each of (H-A1), (H-A2), and (H-A3) comprises sequences of heavy chain complementarity determining regions (CDRHA)-1 comprising an amino acid sequence of SEQ ID NO: 1, CDRHA-2 comprising an amino acid sequence of SEQ ID NO: 2, and CDRHA-3 comprising an amino acid sequence of SEQ ID NO: 3, wherein the CDRHA-1, the CDRHA-2, and the CDRHA-3 sequences are invariant, (2) a heavy chain variable region comprising a polypeptide consisting of the following amino acid sequence (H-B) that is selected from the group consisting of amino acid sequences (H-B1), (H-B2), and (H-B3):

(H-B1) an amino acid sequence of SEQ ID NO: 14, (H-B2) an amino acid sequence having 80% or more identity with respect to the amino acid sequence of SEQ ID NO: 14, and (H-B3) an amino acid sequence in which one to twenty amino acids are deleted, substituted, inserted and/or added in the amino acid sequence of SEQ ID NO: 14, wherein each of (H-B1), (H-B2), and (H-B3) comprises sequences of CDRHB-1 comprising an amino acid sequence of SEQ ID NO: 4, CDRHB-2 comprising an amino acid sequence of SEQ ID NO: 5, and CDRHB-3 comprising an amino acid sequence of SEQ ID NO: 6, wherein the CDRHB-1, the CDRHB-2, and the CDRHB-3 sequences are invariant, (3) a heavy chain variable region comprising a polypeptide consisting of the following amino acid sequence (H-C) that is selected from the group consisting of amino acid sequences (H-C1), (H-C2), and (H-C3):

(H-C1) an amino acid sequence of SEQ ID NO: 15, (H-C2) an amino acid sequence having 80% or more identity with respect to the amino acid sequence of SEQ ID NO: 15, and (H-C3) an amino acid sequence in which one to twenty amino acids are deleted, substituted, inserted and/or added in the amino acid sequence of SEQ ID NO: 15, wherein each of (H-C1), (H-C2), and (H-C3) comprises sequences of CDRHC-1 comprising an amino acid sequence of SEQ ID NO: 7, CDRHC-2 comprising an amino acid sequence of SEQ ID NO: 8, and CDRHC-3 comprising an amino acid sequence of SEQ ID NO: 9, wherein the CDRHC-1, the CDRHC-2, and the CDRHC-3 sequences are invariant, (4) a light chain variable region comprising a polypeptide consisting of the following amino acid sequence (L-A) that is selected from the group consisting of amino acid sequences (L-A1), (L-A2), and (L-A3):

(L-A1) an amino acid sequence of SEQ ID NO: 16, (L-A2) an amino acid sequence having 80% or more identity with respect to the amino acid sequence of SEQ ID NO: 16, and (L-A3) an amino acid sequence in which one to twenty amino acids are deleted, substituted, inserted and/or added in the amino acid sequence of SEQ ID NO: 16, wherein each of (L-A1), (L-A2), and (L-A3) comprises sequences of light chain complementarity determining regions (CDRL)-1 comprising an amino acid sequence of SEQ ID NO: 10, CDRL-2 comprising an amino acid sequence of SEQ ID NO: 11, and CDRL-3 comprising an amino acid sequence of SEQ ID NO: 12, wherein the CDRL-1, the CDRL-2, and the CDRL-3 sequences are invariant.

3. An antibody against Chikungunya virus or an antigen-binding fragment of the antibody, comprising the following heavy chain (1), (2), or (3) and the following light chain (4):

(1) a heavy chain comprising a polypeptide consisting of the following amino acid sequence (HA) that is selected from the group consisting of amino acid sequences (HA1), (HA2), and (HA3):

(HA1) an amino acid sequence of SEQ ID NO: 17, (HA2) an amino acid sequence having 80% or more identity with respect to the amino acid sequence of SEQ ID NO: 17, and (HA3) an amino acid sequence in which one to eighty amino acids are deleted, substituted, inserted and/or added in the amino acid sequence of SEQ ID NO: 17, wherein the SEQ ID NO: 17 comprises sequences of heavy chain complementarity determining regions (CDRHA)-1 comprising an amino acid sequence of SEQ ID NO: 1, CDRHA-2 comprising an amino acid sequence of SEQ ID NO: 2, and CDRHA-3 comprising an amino acid sequence of SEQ ID NO: 3, wherein the CDRHA-1, the CDRHA-2, and the CDRHA-3 sequences are invariant, (2) a heavy chain comprising a polypeptide consisting of the following amino acid sequence (HB) that is selected from the group consisting of amino acid sequences (HB1), (HB2), and (HB3):

(HB1) an amino acid sequence of SEQ ID NO: 18, (HB2) an amino acid sequence having 80% or more identity with respect to the amino acid sequence of SEQ ID NO: 18, and (HB3) an amino acid sequence in which one to eighty amino acids are deleted, substituted, inserted and/or added in the amino acid sequence of SEQ ID NO: 18, wherein the SEQ ID NO: 18 comprises sequences of CDRHB-1 comprising an amino acid sequence of SEQ ID NO: 4, CDRHB-2 comprising an amino acid sequence of SEQ ID NO: 5, and CDRHB-3 comprising an amino acid sequence of SEQ ID NO: 6, wherein the CDRHB-1, the CDRHB-2, and the CDRHB-3 sequences are invariant, (3) a heavy chain comprising a polypeptide consisting of the following amino acid sequence (HC) that is selected from the group consisting of amino acid sequences (HC1), (HC2), and (HC3):

(HC1) an amino acid sequence of SEQ ID NO: 19, (HC2) an amino acid sequence having 80% or more identity with respect to the amino acid sequence of SEQ ID NO: 19, and (HC3) an amino acid sequence in which one to eighty amino acids are deleted, substituted, inserted and/or added in the amino acid sequence of SEQ ID NO: 19, wherein the SEQ ID NO: 19 comprises sequences of CDRHC-1 comprising an amino acid sequence of SEQ ID NO: 7, CDRHC-2 comprising an amino acid sequence of SEQ ID NO: 8, and CDRHC-3 comprising an amino acid sequence of SEQ ID NO: 9, wherein the CDRHC-1, the CDRHC-2, and the CDRHC-3 sequences are invariant, (4) a light chain comprising a polypeptide consisting of the following amino acid sequence (LA) that is selected from the group consisting of amino acid sequences (LA1), (LA2), and (LA3):

(LA1) an amino acid sequence of SEQ ID NO: 20, (LA2) an amino acid sequence having 80% or more identity with respect to the amino acid sequence of SEQ ID NO: 20, and (LA3) an amino acid sequence in which one to forty amino acids are deleted, substituted, inserted and/or added in the amino acid sequence of SEQ ID NO: 20, wherein SEQ ID NO: 20 comprises sequences of light chain complementarity determining regions (CDRL)-1 comprising an amino acid sequence of SEQ ID NO: 10, CDRL-2 comprising an amino acid sequence of SEQ ID NO: 11, and CDRL-3 comprising an amino acid sequence of SEQ ID NO: 12, wherein the CDRL-1, the CDRL-2, and the CDRL-3 sequences are invariant.

4. The antibody against Chikungunya virus or the antigen-binding fragment of the antibody according to claim 1, wherein the antibody binds to an envelope glycoprotein of the Chikungunya virus.

5. A detection kit for Chikungunya virus, comprising:

the antibody or the antigen-binding fragment of the antibody according to claim 1.

6. The detection kit according to claim 5, comprising:

a detection reagent that detects binding between Chikungunya virus and the antibody or the antigen-binding fragment of the antibody.

* * * * *